United States Patent
Bar-Or et al.

(10) Patent No.: US 9,060,968 B2
(45) Date of Patent: *Jun. 23, 2015

(54) TREATMENT OF DEGENERATIVE JOINT DISEASE

(71) Applicant: AMPIO PHARMACEUTICALS, INC., Greenwood Village, CO (US)

(72) Inventors: David Bar-Or, Englewood, CO (US); James V. Winkler, Denver, CO (US)

(73) Assignee: Ampio Pharmaceuticals, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/681,618

(22) Filed: Nov. 20, 2012

(65) Prior Publication Data

US 2013/0090292 A1 Apr. 11, 2013

Related U.S. Application Data

(63) Continuation of application No. PCT/US2012/059455, filed on Oct. 10, 2012.

(60) Provisional application No. 61/545,474, filed on Oct. 10, 2011, provisional application No. 61/561,221, filed on Nov. 17, 2011.

(51) Int. Cl.
| | |
|---|---|
| *A61K 38/00* | (2006.01) |
| *A61P 19/02* | (2006.01) |
| *A61K 38/12* | (2006.01) |
| *A61K 45/06* | (2006.01) |
| *A61K 31/20* | (2006.01) |
| *A61K 31/405* | (2006.01) |

(52) U.S. Cl.
CPC .............. *A61K 38/12* (2013.01); *A61K 45/06* (2013.01); *A61K 31/20* (2013.01); *A61K 31/405* (2013.01)

(58) Field of Classification Search
None
See application file for complete search history.

(56) References Cited

U.S. PATENT DOCUMENTS

| | | | |
|---|---|---|---|
| 3,928,330 A | 12/1975 | Ramey et al. |
| 3,941,790 A | 3/1976 | Creighton |
| 3,976,773 A | 8/1976 | Curran |
| 4,006,261 A | 2/1977 | Pickenhagen et al. |
| 4,088,649 A | 5/1978 | Smith et al. |
| 4,205,057 A | 5/1980 | Whitaker |
| 4,289,759 A | 9/1981 | Heavner et al. |
| 4,312,987 A | 1/1982 | Beck |
| 4,331,595 A | 5/1982 | Heavner et al. |
| 4,661,500 A | 4/1987 | Rozencwaig |
| 4,694,061 A | 9/1987 | Pfeifer |
| 4,694,081 A | 9/1987 | Miller et al. |
| 4,771,056 A | 9/1988 | Rozencwaig |
| 4,806,538 A | 2/1989 | Shimazaki et al. |
| 4,886,796 A | 12/1989 | Eichner et al. |
| 4,940,709 A | 7/1990 | Shimazaki et al. |
| 4,992,552 A | 2/1991 | Hubbs et al. |
| 5,047,401 A | 9/1991 | Lipsky et al. |
| 5,144,073 A | 9/1992 | Hubbs |
| 5,238,938 A | 8/1993 | Tone et al. |
| 5,352,461 A | 10/1994 | Feldstein et al. |
| 5,358,938 A | 10/1994 | Cai et al. |
| 5,418,218 A | 5/1995 | Wilber |
| 5,434,151 A | 7/1995 | Cai et al. |
| 5,463,083 A | 10/1995 | Biftu et al. |
| 5,503,852 A | 4/1996 | Steiner et al. |
| 5,512,544 A | 4/1996 | Wallach et al. |
| 5,538,993 A | 7/1996 | Mechoulam et al. |
| 5,543,402 A | 8/1996 | Bosies et al. |
| 5,543,503 A | 8/1996 | Chuntharapai et al. |
| 5,545,404 A | 8/1996 | Page |
| 5,550,132 A | 8/1996 | Benson et al. |
| 5,578,323 A | 11/1996 | Milstein et al. |
| 5,589,501 A | 12/1996 | Carrera et al. |
| 5,648,486 A | 7/1997 | Cai et al. |
| 5,693,338 A | 12/1997 | Milstein |
| 5,700,804 A | 12/1997 | Collins et al. |
| 5,703,093 A | 12/1997 | Cai et al. |
| 5,741,809 A | 4/1998 | Biftu et al. |
| 5,750,530 A | 5/1998 | Bryans et al. |
| 5,750,565 A | 5/1998 | Cai et al. |
| 5,776,892 A | 7/1998 | Counts et al. |
| 5,780,503 A | 7/1998 | Biftu et al. |
| 5,792,776 A | 8/1998 | Biftu et al. |
| 5,817,751 A | 10/1998 | Szardenings et al. |

(Continued)

FOREIGN PATENT DOCUMENTS

| | | |
|---|---|---|
| CS | 254868 | 6/1987 |
| CZ | 2827.94 | 4/1996 |
| CZ | 280726 | 4/1996 |
| CZ | 2000-2680 | 7/2000 |
| CZ | 2000-2681 | 7/2000 |
| DE | 19937721 | 2/2001 |
| EP | 0043219 | 1/1982 |
| EP | 0214557 | 3/1987 |
| EP | 0216746 | 4/1987 |
| EP | 0220958 | 5/1987 |

(Continued)

OTHER PUBLICATIONS

Millipore User Guide—Centricon®—Centrifugal Filter Devices User Guide (2005). retrieved from: http://kirschner.med.harvard.edu/files/protocols/Millipore_Centricons.pdf.*

(Continued)

*Primary Examiner* — Vanessa L. Ford
*Assistant Examiner* — Sandra Dillahunt
(74) *Attorney, Agent, or Firm* — Sheridan Ross P.C.

(57) ABSTRACT

The invention provides a method of treating a degenerative joint disease. The method comprises administering an effective amount of a pharmaceutical composition comprising a diketopiperazine with amino acid side chains of aspartic acid and alanine (DA-DKP). The invention also provides a pharmaceutical product as well as a kit comprising DA-DKP.

4 Claims, 10 Drawing Sheets

(56) References Cited

U.S. PATENT DOCUMENTS

| | | |
|---|---|---|
| 5,834,032 A | 11/1998 | Song |
| 5,843,950 A | 12/1998 | Tasaka et al. |
| 5,856,323 A | 1/1999 | Cai et al. |
| 5,877,174 A | 3/1999 | Ono et al. |
| 5,883,227 A | 3/1999 | Kline et al. |
| 5,886,152 A | 3/1999 | Nakatani et al. |
| 5,902,812 A | 5/1999 | Brocchini et al. |
| 5,919,785 A | 7/1999 | Dinsmore et al. |
| 5,932,112 A | 8/1999 | Browning, Jr. |
| 5,932,579 A | 8/1999 | Campbell et al. |
| 5,976,569 A | 11/1999 | Milstein |
| 5,985,581 A | 11/1999 | Nixon et al. |
| 5,990,112 A | 11/1999 | Campbell et al. |
| 6,034,057 A | 3/2000 | Dutta |
| 6,034,221 A | 3/2000 | Berezenko et al. |
| 6,060,452 A | 5/2000 | Green et al. |
| 6,090,780 A | 7/2000 | Prasad |
| 6,096,737 A | 8/2000 | Loder |
| 6,099,856 A | 8/2000 | Milstein et al. |
| 6,107,050 A | 8/2000 | Alkon et al. |
| 6,180,616 B1 | 1/2001 | Fukunaga |
| 6,222,029 B1 | 4/2001 | Edwards et al. |
| 6,248,363 B1 | 6/2001 | Patel et al. |
| 6,262,119 B1 | 7/2001 | Ferrante et al. |
| 6,265,535 B1 | 7/2001 | Greene et al. |
| 6,331,318 B1 | 12/2001 | Milstein |
| 6,358,957 B1 | 3/2002 | Fukumoto et al. |
| 6,395,774 B1 | 5/2002 | Milstein |
| 6,441,172 B1 | 8/2002 | Nefzi et al. |
| 6,461,875 B1 | 10/2002 | Bar-Or et al. |
| 6,475,743 B1 | 11/2002 | Bar-Or et al. |
| 6,492,179 B1 | 12/2002 | Bar-Or et al. |
| 6,531,505 B2 | 3/2003 | Xu et al. |
| 6,541,224 B2 | 4/2003 | Yu et al. |
| 6,555,543 B2 | 4/2003 | Bar-Or et al. |
| 6,635,649 B2 | 10/2003 | Teng et al. |
| 6,677,473 B1 | 1/2004 | Madison et al. |
| 6,689,765 B2 | 2/2004 | Baroudy et al. |
| 6,815,214 B2 | 11/2004 | Boyce et al. |
| 6,930,112 B2 | 8/2005 | Weaver et al. |
| 6,967,202 B2 | 11/2005 | Rao et al. |
| 7,026,322 B2 | 4/2006 | Hayashi et al. |
| 7,175,844 B2 | 2/2007 | King |
| 7,276,534 B2 | 10/2007 | Milstein |
| 7,288,545 B2 | 10/2007 | Teng et al. |
| 7,332,153 B2 | 2/2008 | Bhatia et al. |
| 7,378,403 B2 | 5/2008 | Kozikowski et al. |
| 7,575,929 B2 | 8/2009 | Bar-Or et al. |
| 7,732,403 B2 | 6/2010 | Bar-Or et al. |
| 7,919,497 B2 | 4/2011 | Palladino et al. |
| 8,030,488 B2 | 10/2011 | Sviridov et al. |
| 8,067,425 B2 | 11/2011 | Brimble et al. |
| 8,183,209 B2 | 5/2012 | Bar-Or et al. |
| 8,217,047 B2 | 7/2012 | Bar-Or |
| 8,268,830 B2 | 9/2012 | Bar-Or et al. |
| 8,324,167 B2 | 12/2012 | Bar-Or et al. |
| 2003/0119750 A1 | 6/2003 | Demuth et al. |
| 2003/0153575 A1 | 8/2003 | Orme et al. |
| 2003/0157030 A1 | 8/2003 | Davis et al. |
| 2003/0187226 A1 | 10/2003 | Goodey et al. |
| 2003/0203915 A1 | 10/2003 | Fang et al. |
| 2003/0225103 A1 | 12/2003 | Bar-Or et al. |
| 2004/0024180 A1 | 2/2004 | Drauz et al. |
| 2004/0038865 A1 | 2/2004 | Gelber et al. |
| 2004/0063654 A1 | 4/2004 | Davis et al. |
| 2005/0096323 A1 | 5/2005 | Cheng et al. |
| 2005/0249681 A1 | 11/2005 | Heidenfelder et al. |
| 2007/0060508 A1 | 3/2007 | Haberl et al. |
| 2007/0208087 A1 | 9/2007 | Sanders et al. |
| 2008/0009507 A1 | 1/2008 | Cosford et al. |
| 2008/0017576 A1 | 1/2008 | Belfort et al. |
| 2008/0260838 A1 | 10/2008 | Hokenson et al. |
| 2010/0120056 A1 | 5/2010 | Bar-Or et al. |
| 2010/0143338 A1* | 6/2010 | Bar-Or et al. ............. 424/130.1 |
| 2010/0144611 A1 | 6/2010 | Bar-Or et al. |
| 2010/0190696 A1 | 7/2010 | Bar-Or et al. |
| 2012/0022003 A1 | 1/2012 | Bar-Or et al. |
| 2012/0022081 A1 | 1/2012 | Bar-Or et al. |
| 2012/0058934 A1 | 3/2012 | Bar-Or |
| 2012/0094918 A1 | 4/2012 | Bar-Or et al. |
| 2012/0157473 A1 | 6/2012 | Bar-Or |
| 2012/0172294 A1 | 7/2012 | Bar-Or |
| 2013/0303463 A1 | 11/2013 | Bar-Or |
| 2013/0345238 A1 | 12/2013 | Bar-Or et al. |
| 2014/0256642 A1 | 9/2014 | Bar-Or et al. |
| 2014/0286913 A1 | 9/2014 | Bar-Or et al. |
| 2014/0294738 A1 | 10/2014 | Bar-Or |

FOREIGN PATENT DOCUMENTS

| | | |
|---|---|---|
| EP | 0493812 | 7/1992 |
| EP | 0557388 | 9/1993 |
| EP | 0610943 | 8/1994 |
| EP | 0655060 | 5/1995 |
| EP | 0835660 | 4/1998 |
| EP | 0939124 | 9/1999 |
| EP | 1445323 | 8/2004 |
| FR | 2717484 | 9/1995 |
| GB | 2263109 | 7/1993 |
| GB | 2372740 | 9/2002 |
| JP | 59-73574 | 4/1984 |
| JP | 61-112060 | 5/1986 |
| JP | 62-036331 | 2/1987 |
| JP | 63290868 | 11/1988 |
| JP | 01-013075 | 1/1989 |
| JP | 3176478 | 7/1991 |
| JP | 05-163148 | 6/1993 |
| JP | 07-247474 | 9/1995 |
| JP | 08-277203 | 10/1996 |
| JP | 10-226615 | 8/1998 |
| JP | 10245315 | 9/1998 |
| JP | 11-504509 | 4/1999 |
| JP | 2000-327575 | 11/2000 |
| JP | 2002-527753 | 8/2002 |
| NZ | 218088 | 1/1989 |
| NZ | 335544 | 8/2001 |
| RU | 2112242 | 5/1998 |
| RU | 2125728 | 1/1999 |
| RU | 2128840 | 4/1999 |
| WO | WO 91/14378 | 10/1991 |
| WO | WO 93/08815 | 5/1993 |
| WO | WO 94/04512 | 3/1994 |
| WO | WO 94/04513 | 3/1994 |
| WO | WO 94/04537 | 3/1994 |
| WO | WO 94/20063 | 9/1994 |
| WO | WO 95/03054 | 2/1995 |
| WO | WO 95/18610 | 7/1995 |
| WO | WO 96/00212 | 1/1996 |
| WO | WO 96/00391 | 1/1996 |
| WO | WO 96/10396 | 4/1996 |
| WO | WO 96/32478 | 10/1996 |
| WO | WO 97/12625 | 4/1997 |
| WO | WO 97/36888 | 10/1997 |
| WO | WO 97/38011 | 10/1997 |
| WO | WO 97/48685 | 12/1997 |
| WO | WO 98/09968 | 3/1998 |
| WO | WO 98/40748 | 9/1998 |
| WO | WO 99/40931 | 8/1999 |
| WO | WO 99/49865 | 10/1999 |
| WO | WO 99/51256 | 10/1999 |
| WO | WO 99/51720 | 10/1999 |
| WO | WO 00/20454 | 4/2000 |
| WO | WO 00/20840 | 4/2000 |
| WO | WO 00/22439 | 4/2000 |
| WO | WO 00/43000 | 7/2000 |
| WO | WO 00/57187 | 9/2000 |
| WO | WO 01/34586 | 5/2001 |
| WO | WO 01/91713 | 12/2001 |
| WO | WO 02/11676 | 2/2002 |
| WO | WO 02/12201 | 2/2002 |
| WO | WO 02/059604 | 8/2002 |
| WO | WO 02/062797 | 8/2002 |
| WO | WO 02/083667 | 10/2002 |
| WO | WO 02/089738 | 11/2002 |

(56) References Cited

FOREIGN PATENT DOCUMENTS

| WO | WO 03/032809 | 4/2003 |
|---|---|---|
| WO | WO 03/045395 | 6/2003 |
| WO | WO 2004/034060 | 4/2004 |
| WO | WO 2004/048345 | 6/2004 |
| WO | WO 2004/054498 | 7/2004 |
| WO | WO 2004/103304 | 12/2004 |
| WO | WO 2005/011699 | 2/2005 |
| WO | WO 2006/023943 | 3/2006 |
| WO | WO 2007/098500 | 8/2007 |
| WO | WO 2007/121411 | 10/2007 |
| WO | WO 2007/149730 | 12/2007 |
| WO | WO 2008/008357 | 1/2008 |
| WO | WO 2009/009793 | 1/2009 |
| WO | WO 2009/032651 | 3/2009 |
| WO | WO 2009/042193 | 4/2009 |
| WO | WO 2010/102148 | 9/2010 |
| WO | WO 2012/033789 | 3/2012 |

OTHER PUBLICATIONS

Neustadt. Intra-articular injections for osteoarthritis of the knee. Cleveland Clinic Journal of Medicine. 73(10). Oct. 2006.*
Millipore User Guide—Centricon®—Centrifugal Filter Devices User Guide (2005). retrieved from: http://kirschnermed.harvard.edu/files/protocols/Millipore_Centricons.pdf.*
Tascioglu et al. Efficacy of intra-articular sodium hyaluronate in the treatment of knee osteoarthritis. Clinical Rheumatology. 2003; 22:112-117.*
Rutjes et al. Viscosupplementation for osteoarthritis of the knee. Annals of Internal Medicine. 2012; 157(3): 180-192.*
Watterson et al. Viscosupplementation: Therapeutic Mechanisms and Clinical Potential in Osteoarthritis of the Knee. Journal of the American Academy of Orthopaedic Surgeons. 2000; 8 (5): 277-284.*
Kullenberg et al. Intraarticular corticosteroid injection: pain relief in osteoarthrtis of the hip? Journal of Rheumatology. 2004; 31(11):2265-2268.*
Oztuna et al. Intra-articular injection of tenoxicam in osteoarthritic knee joints with effusion. Orthopedics. 2007; 30 (12): 1039-1042.*
Millipore User Guide—Centricon®—Centrifugal Filter Devices User Guide (2005). retrieved from: http://kirschner.med, harvard.edu/files/protocols/Millipore_Centricons.pdf.*
Nakamura et al. T-cell mediated inflammatory pathway in osteoarthritis. Osteoarthritis and Cartilage. 7:401-402, 1999.*
U.S. Appl. No. 13/676,932, filed Nov. 14, 2012, Bar-Or et al.
U.S. Appl. No. 13/676,966, filed Nov. 14, 2012, Bar-Or et al.
U.S. Appl. No. 13/676,984, filed Nov. 14, 2012, Bar-Or et al.
U.S. Appl. No. 13/677,077, filed Nov. 14, 2012, Bar-Or et al.
U.S. Appl. No. 13/679,599, filed Nov. 16, 2012, Bar-Or et al.
"Disposable PD-10 Desalting Columns," GE Healthcare Life Sciences, downloaded Nov. 1, 2011, 2 pages.
"Desalting and buffer exchange with Sephadex® G-25," Amersham Biosciences, downloaded from www.gelifesciences.com on Jan. 8, 2013, 8 pages.
"Human Albumin," Sigma downloaded from www.sigmaaldrich.com on Jan. 8, 2013, 1 page.
"Tryprostatin A, Aspergillus fumigates," available at www.emdbiosciences.com/Products/ProductDisplay.asp?catno=649305&, printed on Jun. 21, 2006, 1 page.
Abraha et al., "C-terminal inhibition of tau assembly in vitro and in Alzheimer's disease," Journal of Cell Science, 2000, vol. 113, pp. 3737-3745.
Acharya et al., "Solid-phase synthesis of substituted imidazoline-tethered 2,3-diketopiperazines, cyclic ureas, and cyclic thioureas," J Comb Chem, Nov.-Dec. 2001, vol. 3(6), pp. 612-623.
Adorini, L., "Selective immunointervention in autoimmune diseases: lessons from multiple sclerosis," J Chemother, Jun. 2001, vol. 13(3), pp. 219-234 (Abstract Only Provided).
Akiyama et al., "Inflammation and Alzheimer's disease," Neurobiol Aging, 2000, vol. 21, pp. 383-421.
Alvarez et al., "Isolation and Structure Elucidation of Two New Calpain Inhibitors from *Streptomyces griseus*," J. Antibiotics, Nov. 1994, vol. 47(11), pp. 1195-1201.
Andreasen et al., "Cerebrospinal fluid beta-amyloid (1-42) in Alzheimer disease: differences between early- and late-onset Alzheimer disease and stability during the course of disease," Arch. Neurol., Jun. 1999, vol. 56(6), pp. 673-680.
Arbabi et al., "Priming Interleukin 8 Production: Role of Platelet-Activating Factor and p38," Arch Surg., Dec. 1999, vol. 134(12), pp. 1348-1353.
Ashwood et al. "Is autism an autoimmune disease?" Autoimmunity Reviews, Nov. 2004, vol. 3, No. 7-8, pp. 557-562.
Au et al., "Effect of PDE4 Inhibitors on Zymosan-Induced IL-8 Release From Human Neutrophils: Synergism with Prostanoids and Salbutamol," Br. J. Pharmacol, 1998, vol. 123, pp. 1260-1266.
Bagaria et al., "Cyclo(L-leucyl-alpha,beta-dehydrophenylalanine): the first diketopiperazine containing an alpha,beta-dehydrophenylalanine residue," Acta Crystallogr C., Mar. 2005, vol. 61(Pt 3), pp. 174-176, Epub Feb. 28, 2005.
Baig et al., "High Performance Liquid Chromatography as a Tool in the Definition of Abnormalities in Monamine and Tryptophan Metabolites in Cerebrospinal Fluid from Patients with Neurological Disorders," Biomed Chromatogr 1991, 5(3):108-112 (Abstract Only Provided).
Balk, "Lesson 24, vol. 12—ARDS: Pathophysiology of SIRS and MODS" www.chestnet.org/education/pccu/vol12/ lesson24.html, pp. 1-19, printed Jul. 20, 2000.
Banks et al., "Radioactively Iodinated Cyclo(His-Pro) Crosses the Blood-Brain Barrier and Reverses Ethanol-Induced Narcosis," Am J Physiol, May 1993, vol. 264(5 Pt. 1), pp. E723-e729 (Abstract Only Provided).
Bar-Or et al., "An Analog of the Human Albumin N-Terminus (Asp-Ala-His-Lys) Prevents Formation of Copper-Induced Reactive Oxygen Species," Biochemical and Biophysical Research Communications, 2001, vol. 284(3), pp. 856-862.
Bar-Or et al. "Commercial human albumin preparations for clinical use are immunosuppressive in vitro," Critical Care Medicine, Jun. 2006, vol. 34, No. 6, pp. 1707-1712 (Abstract Only) (downloaded from : journals.lww.com).
Bar-Or et al., "Potential Plasma Surrogate Biomakers for CNS Demyelinating Processes," 19th Congress of the European Committee for Treatment and Research in Multiple Sclerosis Meeting; Sep. 17-20, 2003; 2 pp. (Abstract first distributed at the meeting; attached is poster presented at meeting).
Barrow et al., WIN 64821, a New Competitive Antagonist to Substance P, Isolated from an *Aspergillus* Species: Structure Determination and Solution Conformation, J. Org. Chem., 1993, vol. 58, pp. 6016-6021.
Battersby et al., "Diketopiperazine Formation and N-Terminal Degradation in Recombinant Human Growth Hormone," Int. J. Pept. Protein Res, Sep. 1994, vol. 44(3), pp. 215-222 (Abstract Only Provided).
Berry et al., "Inhibition of Tau Polymerization by its Carboxy-Terminal Caspase Cleavage Fragment," Biochemistry, 2003, vol. 42, pp. 8325-8331.
Bhargava et al., "Inhibition of Neuroleptic-Induced Dopamine Receptor Supersensitivity by Cyclo (Leu-Gly)," Pharmacol Biochem Behav, Nov. 1980, vol. 13(5), pp. 633-636 (Abstract Only Provided).
Bhargava, "Antagonism of ketamine-induced anesthesia and hypothermia by thyrotropin releasing hormone and cyclo (His-Pro)," Neuropharmacology, 1981, vol. 20(7), pp. 699-702.
Bhargava, "Inhibition of abstinence syndrome in opiate dependent mice by cyclo (His-Pro)," Life Sci, 1981, vol. 28(11), pp. 1261-1267.
Bhargava, "The effect of melanotrophin release inhibiting factor (MIF) and cyclo (Leu-Gly) on the tolerance to morphine-induced antinociception in the rat: a dose-response study," Br J Pharmacol, Apr. 1981, vol. 72(4) (Abstract Only Provided).
Bhargava, "The effects of thyrotropin releasing hormone and histidyl-proline diketopiperazine on delta-9-tetrahydrocannabinol-induced hypothermia," Life Sci, 1980, vol. 26(11), pp. 845-850.
Bielekova et al., "Development of biomarkers in multiple sclerosis," Brain, Jul. 2004, vol. 127(Pt 7), pp. 1463-1478, Epub Jun. 4, 2004.

(56) References Cited

OTHER PUBLICATIONS

Binisti et al., "Structure-Activity Relationships in Platelet Activating Factor," J. Lipid Mediat. Cell Signal, Jan. 1997, vol. 15(2), pp. 125-144 (Abstract Only Provided).
Blazickova et al., "Immunomodulatory Characteristics of Synthetic Cyclic Dipeptides," Int. J. Immunotherapy, 1994, vol. 10(3), pp. 89-93.
Bowden et al., "Re-evaluation of histidyl-proline diketopiperazine [cyclo (His-Pro)] effects on food intake in the rate," Pharmacol. Biochem. Behav., Feb. 1988, vol. 29(2), pp. 357-363 (Abstract Only Provided).
Brauns et al., "Selected cyclic dipeptides inhibit cancer cell growth and induce apoptosis in HT-29 colon cancer cells," Anticancer Research, 2004, vol. 24, pp. 1713-1720.
Bressan et al., "Coordination chemistry of peptides. Part II. Crystal structure of cyclo-L-methionylglycine and studies of metal complexation," Int J Pept Protein Res, Apr. 1982, vol. 19(4) (Abstract Only Provided).
Bresser et al., "T-Cell Activation in the Lungs of Patients With Systemic Sclerosis and Its Relation With Pulmonary Fibrosis," Chest, Jul. 2001, 6 pages.
Bunn, "Early detection of lung cancer using serum RNA or DNA markers: ready for "prime time" or for validation?," J Clin Oncol., Nov. 1, 2003, vol. 21(21), pp. 3891-3893.
Caballero et al., "Brief synthesis of the cell cycle inhibitor tryprostatin B and its alanine analogue," Fourth International Electronic conference of Synthetic Organic Chemistry (ECXOC-4), Sep. 1-13, 2000, 4 pages, available at page.unibas.ch/mdpi/eecxoc-4/c0023/c0023.htm.
Caballero et al., "Brief total synthesis of the cell cycle inhibitor tryprostatin B and related preparation of its alanine analogue," J Org Chem, Sep. 5, 2003, vol. 68(18) (Abstract Only Provided).
Carlton et al., "Attenuation of alcohol-induced hypothermia by cycle (His-Pro) and its analogs," Neuropeptides, Jun. 1995, vol. 28(6), pp. 351-355 (Abstract Only Provided).
Chan et al., "Site-Specific N-Terminal Auto-Degradation of Human Serum Albumin," Eur. J. Biochem., 1995, vol. 227, pp. 524-528.
Chen et al., "Up-regulation of Platelet-activating Factor Receptors in Lung and Alveolar Macrophages in the Bleomycin-Hamster Model of Pulmonary Fibrosis," J. Pharmacol. Exp. Ther., 1997, vol. 280(3), pp. 1219-1227.
Cho et al., "Contribution of Natural Inhibitors to the Understanding of the PI3K/PDK1/PKB Pathway in the Insulin-mediated Intracellular Signaling Cascade," Int. J. Mol. Sci., 2008, vol. 9, pp. 2217-2230.
Ciarkowski et al., "Conformation of cyclo-(D-phenylalanyl-trans-4-fluoro-D-prolyl)," Int. J. Pept. Protein Res., vol. 36, Sep. 1990, pp. 285-291.
Clark et al., "Roquefortine E, a Diketopiperazine from an Australian Isolate of Gymnoascus reessii," J. Nat. Prod., 2005, vol. 68(11), p. 1661-1664 (Abstract Only Provided).
Cody et al., "The design of potent and selective inhibitors of thrombin utilizing a piperazinedione template: part 2," Bioorg Med Chem Lett, Sep. 6, 1999, vol. 9(17), pp. 2503-2508.
Coggins et al., "High Affinity Specific Binding of the Thyrotrophin Releasing Hormone Metabolite Histidylproline to Rat Brain Membranes," Neuropeptides, Jan. 1987, vol. 9(1), pp. 83-91 (Abstract Only Provided).
Couladouros et al., "Solid-phase total synthesis of (-)-Phenylhistine and (-)-Aurantiamine. Synthesis of a diverse dehydro-2,5-diketopiperazine library. Part II," Mol Divers., 2005, vol. 9(1-3), pp. 111-121.
Crowe et al., "The N Terminal Region of Human Tau is Present in Alzheimer's Disease Protein A68 and is Incorporated into Paired Helical Filaments," American Journal of Pathology, 1991, vol. 139(6), pp. 1463-1470.
Cruse et al., "Illustrated Dictionary of Immunology" Second Edition, 2003, pp. 192, 260, 530-531.
Cui et al., "Novel Mammalian Cell Cycle Inhibitors, Tryprostatins A, B and Other Diketopiperazines Produced by *Aspergillus fumigatus* II. Physico-chemical properties and Structures," The Journal of Antibiotics, Jun. 1996, pp. 534-540.
Cytokines and Autoimmune Diseases, edited by Kuchroo, et al., 2002, Humana Press Inc., Totowa, NJ, pp. 3-23, 389-406.
Cytokines and Autoimmune Diseases, edited by Kuchroo, et al., 2002, Humana Press Inc., Totowa, NJ, pp. 5, 11, and 391.
Database WPI Section Ch, Week 199844 Derwent Publications Ltd., London, GB; Class B03, AN 1998-515050 XP002369751 & JP 10 226615 A (Pola Chem Ind Inc) Aug. 25, 1998.
D'Alagni et al. "Effect of Urea on the Optical Rotatory Dispersion of Diketopiperazines of I-Serine, I-Alanine, I-Lysine, I-Valine, and I-Valylglycine." The Journal of Biological Chemistry, Nov. 10, 1969, vol. 244, No. 21, pp. 5843-5848.
Davidson et al., "Autoimmune Diseases," N. Engl. J. Med, 2001, vol. 345(5), pp. 340-350.
Degrassi et al., "Plant Growth-Promoting *Pseudomonas putida* WCS358 Produces and Secretes Four Cyclic Dipeptides: Cross-Talk with Quorum Sensing Bacterial Sensors," Current Microbiology, 2002, vol. 45, pp. 250-254.
Denault et al., "Transcriptional activation of the interleukin-8 gene by platelet-activating factor in human peripheral blood monocytes," Immunology, 1997, vol. 91, pp. 297-302.
Diamanti et al., "Distribution and Characterization of Cyclo (His-Pro)-like Immunoreactivity in the Human Gastrointestinal Tract," Neuropeptides, Mar. 1985, vol. 6(1):21-5 (Abstract Only Provided).
Duntas et al., "A Fast Protein Liquid Chromatography (FPLC) Method for Study of Thyrotropin-releasing Hormone (TRH) and its metabolite Histidyl-Proline Diketopiperazine (CHP) in Human Blood: Degradation in Liver and Pancreatic Diseases," Neuropeptides, 1993, vol. 25(6), pp. 357-361 (Abstract Only Provided).
Esposito et al., "The Solution Structure of the C-Terminal Segment of Tau Protein," Journal of Peptide Science, 2000, vol. 6, pp. 550-559.
Evans et al. "Metabolic effects of platelet-activating factor in rats in vivo: Stimulation of hepatic glycogenolysis and lipogenesis." Biochemical Journal, Jul. 1990, vol. 269, No. 1, pp. 269-272.
Faden et al., "Neuroprotective and nootropic actions of a novel cyclized dipeptide after controlled cortical impact injury in mice." J. Cerebral Blood Flow & Metabolism, 2003, vol. 23, pp. 355-363.
Faden et al., "Novel diketopiperazine enhances motor and cognitive recovery after traumatic brain injury in rats and shows neuroprotection in vitro and in vivo," J. Cerebral Blood Flow & Metabolism, 2003, vol. 23, pp. 342-354.
Faden et al., "Novel neuroprotective Tripeptides and Dipeptides," Ann. N.Y. Acad. Sci, 2005, vol. 1053, pp. 472-481.
Faden et al., "Novel small peptides with neuroprotective and nootropic properties," J. Alzheimer's Dis, 2004, vol. 6, pp. S93-S97.
Faden et al., "Novel TRH analog improves motor and cognitive recovery after traumatic brain injury in rodents," Am J Physiol, Oct. 1999, vol. 277(4 Pt 2), pp. R1196-R1204.
Fdhila et al., "dd-diketopiperazines: antibiotics active against *Vibrio anguillarum* isolated form marine bacteria associted with cultures of *Pecten maximus*" J Nat Prod, Oct. 2003, vol. 66(10) (Abstract Only Provided).
Fischer, "Diketopiperazines in Peptide and Combinatorial Chemistry," Journal of Peptide Science, 2003, vol. 9, pp. 9-35.
Folkes et al., "Synthesis and in vitro evaluation of a series of diketopiperazine inhibitors of plasminogen activator inhibitor-1," Bioorg Med Chem Lett, Oct. 2001, vol. 11(19), pp. 2589-2592 (Abstract Only Provided).
Fragner et al., "A New Biological Contribution of Cyclo(His-Pro) to the Peripheral Inhibition of Pancreatic Secretion," Am J Physiol, Dec. 1997, vol. 273(6 Pt. 1), pp. E1127-E1132 (Abstract Only Provided).
Gamblin et al., "Tau Polymerization: Role of the Amino Terminus," Biochemistry, 2003, vol. 42(7), pp. 2252-2257.
Garcia-Sierra et al., "Conformational Changes and Truncation of Tau Protein during Tangle Evolution in Alzheimer's Disease," Journal of Alzheimer's Disease, 2003, vol. 5, pp. 65-77.

(56) References Cited

OTHER PUBLICATIONS

Goolcharran et al., "Comparison of the Rates of Deamidation, Diketopiperazine Formation and Oxidation in Recombinant Human Vascular Endothelial Growth Factor and Model Peptides," AAPS PharmSci, 2000 vol. 2(1), p. E5 (Abstract Only Provided).
Gorbitz CH, "Crystal and Molecular Structure of cyclo-L-Aspartyl-L-alanyl (3,6-Dioxo-5-methyl-2-piperazineacetic acid)," Accession No. 1987:598911, Nov. 27, 1987, 1 page (Abstract).
Gorbitz, "Crystal and molecular structures of the isomeric dipeptides alpha-L-aspartyl-L-alanine and beta-L-aspartyl-L-alanine," Acta Chem Scand B., vol. 41(9), Oct. 1987, pp. 679-685.
Gorbitz "Crystal and Molecular Structure of cyclo-L-Aspartyl-L-alanyl (3,6-Dioxo-5-methyl-2-piperazineacetic acid)" Acta Chemica Scandinavica B, 1987, vol. 41, pp. 83-86.
Gordon et al, "Reductive Alkylation on a Solid Phase: Synthesis of a Piperazinedione Combinatorial Library," Bioorganic & Medicinal Chemistry Letters, 1995, vol. 5, No. 1, p. 47-50.
Gountopoulou et al. "TNFα is a potent inducer of platelet-activating factor synthesis in adipocytes but not in preadipocytes. Differential regulation by PI3K." Cytokine, Jan. 2008, vol. 41, No. 2 p. 174-181, (Abstract Only).
Graz et al "Cyclic Dipeptides in the Induction of Maturation for Cancer Therapy," J. Pharm. Pharmacol., 2000, vol. 52, pp. 75-82.
Graz et al., "Mechanism of a anti-fungal action of selected cyclic dipeptides," Pharmazie, Nov. 2001, vol. 56(11), pp. 900-901.
Gross et al., "Regulation of Interleukin-8 Production in a Human Colon Epithelial Cell Line (HT-29)," Gastroenterology, 1995, vol. 108, pp. 653-661.
Grubek-Jaworska et al., "CD4/CD8 lymphocytes in BALF during the efferent phase of lung delayed-type hypersensitivity reaction induced by single antigen inhalation," Med Sci Monit, Sep.-Oct. 2001, vol. 7(5), pp. 878-883 (Abstract Only Provided).
Gu et al., "Diketopiperazine Formation, Hydrolysis, and Epimerization of the New Dipeptide Angiotensin-Converting Enzyme Inhibitor RS-10085," Pharm Res, 1987, vol. 4(5), pp. 392-397 (Abstract Only Provided).
Gudasheva et al., "Anxiolytic activity of endogenous nootropic dipeptide cycloprolylglycine in elevated plus-maze test," Bull Exp Biol Med, May 2001, vol. 131(5) (Abstract Only Provided).
Gudasheva et al., "Identification of a novel endogenous memory facilitating cyclic dipeptide cyclo-prolylglycine in rat brain," FEBS Lett, Aug. 5, 1996, vol. 391(1-2) (Abstract Only Provided).
Guerra et al., "PEGylation Prevents the N-Terminal Degradation of Megakaryocyte Growth and Development Factor," Pharm Res, 1998, vol. 15(12), pp. 1822-1827 (Abstract Only Provided).
Gustafson, "Adipose Tissue, Inflammation and Atherosclerosis," J. Atheroscler. Thromb., Apr. 30, 2010, vol. 17(4), pp. 332-341.
Hansel et al. "Metabolic Syndrome Is Associated with Elevated Oxidative Stress and Dysfunctional Dense High-Density Lipoprotein Particles Displaying Impaired Antioxidative Activity." The Journal of Clinical Endocrinology & Metabolism, Oct. 2004, vol. 89, No. 10, pp. 4963-4971.
Hasegawa et al., "Protein Sequence and Mass Spectrometric Analysis of Tau in the Alzheimer's Disease Brain," Journal of Biological Chemistry, 1992, vol. 267(24), pp. 17047-17054.
Hayashi et al., "Synthetic Hexa- and Heptapeptides That Inhibit IL-8 from Binding to and Activating Human Blood Neutrophils1," J. Immunol., 1995, vol. 154, pp. 814-824.
Hilton et al., "Food Contains the Bioactive Peptide, Cyclo(His-Pro)," J. Clin Endocrinol Metab, Aug. 1992, vol. 75(2), pp. 375-378 (Abstract Only Provided).
Hilton et al., "Identification and Characterization of Cyclo (His-Pro)-Like Immunoreactivity in Amniotic Fluid," Peptides, Mar.-Apr. 1989, vol. 10(2), pp. 299-301 (Abstract Only Provided).
Hilton et al., "Radioimmunoassay of Cyclo(His-Pro) in Unextracted Human Plasma: Report of a Normal Range and Definition of Factors Critical for Successful Assay," Neuropeptides, 1989, vol. 13(1), pp. 65-70 (Abstract Only Provided).
Hilton et al., "Relationship between Plasma Cyclo (His-Pro), a Neuropeptide Common to Processed Protein-Rich Food, C-Peptide/Insulin Molar Ratio in Obese Women," Nutr Neurosci, 2001, vol. 4(6), pp. 469-474 (Abstract Only Provided).
Hlinak et al., "Effect of alaptide, its analogues and oxiracetam on memory for an elevated plus-maze in mice," European Journal of Pharmacology, 1996, vol. 314, pp. 1-7.
Hoffman et al., "An Enzymatically Stable Peptide with activity in the Central Nervous System: Its Penetration through the Blood-CSF Barrier," Brain Res, Feb. 11, 1977, vol. 122(1), pp. 87-94 (Abstract Only Provided).
Holden et al., "Quorum-sensing cross talk: isolation and chemical characterization of cyclic dipeptides from *Pseudomonas aeruginosa* and other Gram-negative bacteria," Moleclur Microbiology, 1999, vol. 33(6), pp. 1254-1266.
Hong et al., "Inhibitory effect against Akt of cyclic dipeptides isolated from *Bacillus* sp" J. Microbiol. Biotechnol., 18, 682-685 (2008).
Houston et al., "The cyclic dipeptide CI-4 [cyclo-(I-Arg-d-Pro)] inhibits family 18 chitinases by structural mimicry of a reaction intermediate," Biochem J., Nov. 15, 2002, vol. 368(Pt 1) (Abstract Only Provided).
Hwang et al., "Effects of cyclo (his-pro) plus zinc on glucose metabolism in genetically diabetic obse mice," Diabetes Obes. Metab., Sep. 2003, vol. 5(5), pp. 317-324 (Abstract Only Provided).
Iriuchijima et al., "Thyrotripin-Releasing Hormone and Cyclo (His-Pro)-Like Immunoreactivities in the Cerebrospinal Fluids of 'Normal' Infants and Adults, and Patients with Various Neuropsychiatric and Neurologic Disorders," Life Sci. 1987, 41(22):2419-2428, Abstract only, from PubMed—PMID:2891013.
Ishibashi et al., "A Mechanism for Bitter Taste Sensibility in Peptides," Agric. Biol. Chem., 1988, vol. 52(3), pp. 819-827.
Ishibashi et al., "Bitterness of Leucine-Containing Peptides," Agric. Biol. Chem., 1987, vol. 51 (9), pp. 2389-2394.
Ishii, et al. "Incidence of brain tumors in rats fed aspartame," Toxicology Letters, 1981, vol. 7, pp. 433-437.
Iyer et al. "Inflammatory lipid mediators in adipocyte function and obesity." Nature Reviews Endocrinology, Feb. 2010, vol. 6, pp. 71-82.
Jackson et al., "Amyotrophic Lateral Sclerosis: Thryrotropin-releasing hormone and histidyl proline diketopiperazine in the spinal cord and cerebrospinal fluid," Neurology, 1986, vol. 36(9), pp. 1218-1223.
Jamie et al., "The effect of the isomers of cyclo(Trp-Pro) on heart and ion-channel activity," J Pharm Pharmacol, Dec. 2002, vol. 54(12) (Abstract Only Provided).
Jara et al., "Elevated serum levels of cyclo (His-Pro), and endogenous inhibitor ofpituitary prolactin secretion, in systemic lupus erythematosus patients," Lupus, 1997, vol. 6(3) (Abstract Only Provided).
Jaspan et al., "Study of Passage of Peptides Across the Blood-Brain Barrier: Biological Effects of Cyclo(His-Pro) After Intravenous and Oral Administration," Annals of the New York Academy of Science, 1994, vol. 739, pp. 101-107 (Abstract Only Provided).
Jiang et al., "AKT signaling in regulating angiogenesis," Current Cancer Drug Targets, 2008, vol. 8, pp. 19-26.
Jiang et al. "Asymmetric Reformastky reaction catalyzed by amino acid derivatives," Huaxue Tongbao CKNI, 2001, vol. 10, pp. 637-640 (English Abstract).
Jicha et al., "Sequence Requirements for Formation of Conformational Variants of Tau Similar to Those Found in Alzheimer's Disease," Journal of Neuroscience Research, 1999, vol. 55, pp. 713-723.
Kaakkola et al., "Effects of two diketopiperazines, cyclo (His-Pro) and cyclo (Asp-Phe), on striatal dopamine: A microdialysis study," Brain Research Bulletin, 1993, vol. 32(6), pp. 667-672.
Kanzaki et al., "Enzymatic synthesis of dehydro cyclo(His-Phe)s, analogs of the potent cell cycle inhibitor, dehydrophenylahistin, and their inhibitory activities toward cell division," Biosci Biotechnol Biochem, Nov. 2004, vol. 68(11), pp. 2341-2345 (Abstract Only Provided).
Kasperska-Zajac et al. "Platelet Activating Factor as a Mediator and Therapeutic Approach in Bronchial Asthma." Inflammation, Apr. 2008, vol. 31, No. 2, pp. 112-120.

(56) References Cited

OTHER PUBLICATIONS

Kikwai et al, "Stability and degradation profiles of Spantide II in aqueous solutions," Eur J Pharm Sci, Feb. 2006, vol. 27(2-3), pp. 158-166, Epub Nov. 2, 2005. (Abstract Only Provided).

Kilian et al., "Biological activity of selected tyrosine-containing 2,5-diketopiperazines," Pharmazie, Apr. 2005, vol. 60(4), pp. 305-309 (Abstract Only Provided).

Kilian et al., "The effect of the isomer of cyclo(Trp-Pro) on heart and ion-channel activity," J. Pharm. Pharmacol., Dec. 2002, vol. 54(12), pp. 1659-1665 (Abstract Only Provided).

Kopple et al. "Conformation of Cyclo-(l-Threonine)2 and Cyclo-(l-Allo Threonine)2 : A Proton and Carbon N.m.r. Study." International Journal of Peptide Protein Research, Jul. 1981, vol. 18, No. 1, pp. 33-40.

Koskinen, "Effect of Low Intravenous Doses of TRH, Acid-TRH and Cyclo (His-Pro) on Cerebral and Peripheral Blood Flows," British Journal of Pharmacology, 1986, vol. 87(3), pp. 509-519 (Abstract Only Provided).

Kow et al., "The Effects of the TRH Metabolite Cyclo(His-Pro) and Its Analogs on Feeding," Pharmacology, Biochemistry & Behavior, 1991, vol. 38, pp. 359-364.

Kuenz et al., "Plasma levels of soluble adhesion molecules sPECAM-1, sP-selectin and sE-selectin are associated with relapsing-remitting disease course of multiple sclerosis," J. Neuroimmunol, Oct. 2005, vol. 167(1-2), pp. 143-149.

Kulikov et al., "Review: The Bioregulatory Role of Platelet-Activating Factor in Intracellular Processes and Cell—Cell Interactions," 1997, www.protein.bio.msu.su/biokhimiya/contents/v63/full/63010057.html, pp. 1-13.

Kurahashi et al., "Histydyl-Proline Diketopiperazine (HPD), a Metabolite of Thyrotropin-Releasing Hormone (TRH), Improves the Ataxic Gait in 3-Acetylpyridine (3-AP) Treated Rats," No To Shinkei, Sep. 1986, vol. 38(9), pp. 893-898 (Abstract Only Provided).

Larsen et al. "Kinetics of degradation and oil solubility of ester prodrugs of a model dipeptide (Gly-Phe)," Eur J Pharm Sci, Aug. 2004, vol. 22(5), pp. 399-408 (Abstract Only Provided).

Lechan et al., "Thyrotropin Releasing Hormone but not Histidyl-Proline Diketopiperazine is Depleted from Rat Spinal Cord Following 5,7-Dihydroxytryptamine Treatment," Brain Research, 1985, vol. 326(1), pp. 152-155 (Abstract Only Provided).

Lechin et al., "Plasma Neurotransmitters and Cortisol in Chronic Illness: Role of Stress," J Medicine, 1994, vol. 25(3-4), pp. 181-192 (Abstract Only Provided).

Leduque et al., "Histidyl-Proline Diketopiperazine (His-Pro DKP) Immunoreactivity is Present in the Glucagon-Containing Cells of the Human Fetal Pancreas," J Clin Invest, 1987, 79(3):875-880 (Abstract Only Provided).

Lee et al., "Cyclo (Leu-Gly attenuates the striatal dopaminergic supersensitivity induced by chronic morphine," Alcohol Drugs Res, 1987, vol. 7(1) (Abstract Only Provided).

Lehninger et al., "Amino Acids and Peptides," Chapter 5 of Principles of Biochemistry, 1993, 2nd edition, pp. 111-133.

Lindner et al., "[Effects of cyclic adenosine-3',5'-monophosphate and cyclo{Lys-Pro}.HCI neuronotrophic factors in tissue culture]," J Hirnforsch, 1987, vol. 28(3) (Abstract Only Provided).

Liu et al., "Hydroxyprolylserine derivatives JBP923 and JBP485 exhibit the antihepatitis activities after gastrointestinal absorption in rats," J Pharmacol Exp Ther, Aug. 2000, vol. 294(2) (Abstract Only Provided).

Luca et al., "Determination of serotonin content and ceruloplasmin activity, of blood and CSF amino acide level in multiple sclerosis," Neurol Psychiatr (Bucur), 1986, vol. 24(3), pp. 153-159.

Lucietto et al., "The biological activity of the histidine-containing diketopiperazines cyclo (His-Ala) and cyclo (His-Gly)," Peptides, Nov. 2006, vol. 27(11), pp. 2706-2714, Epub Jun. 21, 2006 (Abstract Only Provided).

Mayer, "Immunology—Chapter Four," Immunoglobulins—Structure and Function, online at pathmicro.med.sc.edu/mayer/IgStruct2000.htm, University of South Carolina School of Medicine, Nov. 6, 2009, 8 pages.

Mazza et al., "Potential energy calculations on phenylalanine rotamers in different boat forms of proline-containing cyclic dipeptides," Int. J. Pept. Protein Res., vol. 31, Feb. 1988, pp. 157-163.

McCain et al., "Endorphinergic modulation of immune function: potent action of the dipeptide glycyl-L-glutamine," Life Science, 1987, vol. 41, pp. 169-176.

McCain et al., "Modulation of Human T-Cell Suppressor Activity by Beta Endorphin and Glycyl-L-Glutamine," Int. J. Immunopharmoc, 1986, vol. 8(4), pp. 443-446.

McCleland et al., "An investigation into the biological activity of the selected histidine-containing diketopieperazines cyclo(His-Phe) and cyclo(His-Tyr)," Journal of Pharmacy and Pharmacology, Sep. 2004, vol. 56(9), pp. 1143-1153.

Meester et al., "In Vivo Inhibition of Dipeptidyl Peptidase IV Activity by Pro-Pro-diphenyl-phosphonate (Prodipine)," Biochemical Pharmacology, 1997, vol. 54, pp. 173-179.

Mentlein et al., "Dipeptidyl-Peptidase IV Hydrolyses Gastric Inhibitory Polypeptide, Glucagon-Like Peptide-1(7-36)amide, Peptide Histidine Methionine and is Responsible for their Degradation in Human Serum," European Journal of Biochemistry, 1993, vol. 214(3), pp. 829-835 (Abstract Only Provided).

Mesh, "Autoimmune Diseases," internet document <<www.ncbi.nlm.nih.gov/sites/entrez>>, accessed Oct. 31, 2007, 2 pages.

Michell et al., "Biomarkers and Parkinson's Disease," Brain, Aug. 2004, vol. 127, pp. 1693-1705.

Miller et al., "Peptide Inhibitor of Interleukin-8 (IL-8) Reduces Staphylococcal Enterotoxin-A (SEA) Induced Neutrophil Trafficking to the Lung," Inflamm. Res., 1996, vol. 45, pp. 393-397.

Milne, et al. "The biological activity of selected cyclic dipeptides," J. Pharm. Pharmacol., 1998, vol. 50, pp. 1331-1337.

Minelli et al., "Phosphoproteomic analysis of the effect of cyclo-[His-Pro] dipeptide on PC12 cells." Peptides, Jan. 2006;27(1):105-13. Epub Aug. 30, 2005., Abstract only PMID: 16137790.

Mitsuma et al., "Radioimmunoassay for Thyrotropin-Releasing Hormone Precursor Peptide, Lys-Arg-Gln-His-Pro-Gly-Arg-Arg," Exp Clin Endocrinology, 1989, vol. 93(1), pp. 53-60 (Abstract Only Provided).

Mizuma et al., "Concentration-Dependent Preferences of Absorptive and Excretive Transport Cause Atypical Intestinal Absorption of Cyclic Phenylalanylserine: Small Intestine Acts as an Interface Between the Body and Ingested Compounds," Research Communications in Molecular Pathology and Pharmacology, 2002, vol. 111, pp. 199-209.

Mizuma et al., "Intestinal Absorption of Stable Cyclic Glycylphenylalanine: Comparison with the Linear Form," J. Pharm. Pharmacol., 1997, vol. 49, pp. 1067-1071.

Molodavkin et al., "[Effect of the novel dipeptide nootropic agent noopept and its metabolite cyclo-L-prolylglycine on the transcallosal evoked potential in the rat brain]," Eksp Klin Farmakol, Mar.-Apr. 2002, vol. 65(2) (Abstract Only Provided).

Monaco et al., "Plasma and cerebrospinal fluid tryptophan in Multiple Sclerosis and Degenerative Diseases," J Neurol Neurosurg Psychiatry, 1979, vol. 42(7), pp. 640-641 (Abstract Only Provided).

Montine et al., "Cerebrospinal Fluid Ab42, Tau, and F2-Isoprostane Concentrations in Patients with Alzheimer Disease, Other Dementias, and in Age-Matched Controls," Acrch Pathol Lab. Med, Apr. 2001, vol. 125, pp. 510-512.

Mori et al., "Alteration by Liquid Protein Diet of TRH and Cyclo(His-Pro) in the Young Rat Brain," Res. Commun Chem Pathol Pharmacol, 1985, vol. 47(1), pp. 157-160 (Abstract Only Provided).

Mori et al., "Brain TRH and Cyclo (His-Pro) and Brain Protein in the Newborn Rat are Altered by Maternal Liquid Protein Feeding," Life Sci, 1983, vol. 32(14), pp. 1607-1612 (Abstract Only Provided).

Mori et al., "Distribution of histidyl-proline diketopiperazine [cyclo (His-Pro)] and thyrotropin-releasing hormone (TRH) in the primate central nervous system," Brain Res, 1982, vol. 245(1), pp. 183-186.

(56) References Cited

OTHER PUBLICATIONS

Mori et al., "Histidyl-Proline Diketopiperazine Cyclo (His-Pro): Identification and Characterization in Rat Pancreatic Islets," Biochem Biophys Res Commun, 1983, vol. 115(1), pp. 281-286 (Abstract Only Provided).
Mori et al., "Histidyl-Proline Diketopiperazine cyclo (His-Pro): measurement by radioimmunoassay in human blood in normal subject and in patients with hyper- and hypothyroidism," Biochem Biophys Res Commun, 1982, vol. 109(2), pp. 541-547.
Mori et al., "Regional Dissociation of Histidyl-Proline Diketopiperazine (Cyclo-(His-Pro)) and Thyrotropin-Releasing Hormone (TRH) in the Rat Brain," Brain Research, 1982, vol. 231(2), pp. 451-453 (Abstract Only Provided).
Mori et al., "Specific Radioimmunoassay of Cyclo (His-Pro), a Biologically Active Metabolite of Thyrotropin-Releasing Hormone," Endocrinology, 1981, vol. 108(5), pp. 1995-1997 (Abstract Only Provided).
Mori et al., ["TRH and Cyclo (His-Pro) Concentrations in the Young Rat Brain are Altered by a Liquid Protein Diet]," [Article in Japanese], Nippon Naibunpi Gakkai Zasshi, 1987, vol. 63(7), pp. 846-852 (English Abstract Only).
Morley et al., "Neuropeptides and appetite: contribution of neuropharmacological modeling," Fed. Proc., Nov. 1984, vol. 43(14), pp. 2903-2907 (Abstract Only Provided).
Moss et al. "Th1/Th2 cells in inflammatory disease sates: therapeutic implications," Expert Opinion on Biological Therapy, Dec. 2004, vol. 4, No. 12, pp. 1887-1896.
Moss et al., "Kinetics and Mechanism of the Facile Cyclization of Histidyl-Prolineamide to Cyclo (His-Pro) in Aqueous Solution and the Competitive Influence of Human Plasma," J Pharm Pharmacol, 1990, vol. 42(1), pp. 7-12 (Abstract Only Provided).
Murray et al., "Role of α-Synuclein Carboxy-Terminus on Fibril Formation in Vitro," Biochemistry, 2003, vol. 42, pp. 8530-8540.
Nicholson et al., "NPI-2358 is a tubulin-depolymerizing agent: in-vitro evidence for activity as a tumor vascular-disrupting agent," Anticancer Drugs, Jan. 2006, vol. 17(1), pp. 25-31 (Abstract Only Provided).
Nitecki et al., "A Simple Route to Sterically Pure Kiketopiperazines" J. Org. Chem., 1968, vol. 33(2), pp. 864-866.
Online Medical Dictionary definition of albumin, medical-dictionary.thefreedictionary.com/albumin, downloaded Nov. 1, 2011, 4 pages.
Ostrovskaia et al., "Multicomponent antithrombotic effect of the neuroprotective prolyl dipeptide GVS-111 and its major metabolite cyclo-L-prolylglycine," Eksp Klin Farmakol, Mar.-Apr. 2002, vol. 65(2) (Abstract Only Provided).
Palace et al. "Epilepsy: an autoimmune disease?" Journal of Neurology, Neurosurgery & Psychiatry, Dec. 2000, vol. 69, No. 6, pp. 711-714.
Palacios et al., "Tenidap Decreases IL-8 and Monocyte Chemotactic Peptide-1 (MCP-1) mRNA Expression in the Synovial Tissue of Rabbits with Antigen Arthritis and in Cultured Synovial Cells," Clin. Exp. Immunol., 1998, vol. 111, pp. 588-596.
Pandey et al., "Synthetic Peptides Corresponding to a Repetitive Sequence of Malarial Histidine Rich Protein Bind Haem and Inhibit Haemozoin Formation in vitro," Mol Biochem Parasitol, 1997, vol. 90(1), pp. 281-287 (Abstract Only Provided).
Parker et al., "Evidence for the Presence of Immunoreactive Histidyl-Proline Diketopiperazine [Cyclo (His-Pro)] in the Adult Human Brain," Peptides, Nov.-Dec. 1983, vol. 4(6), pp. 879-881 (Abstract Only Provided).
Pekary et al., "In vitro Production of a TRH-Homologous Peptide and His-Pro Diketopiperazine by Human Semen," J Androl, 1985, vol. 6(6), pp. 379-385 (Abstract Only Provided).
Potocka et al., "Pharmacokinetic characterization of the novel pulmonary delivery excipient fumaryl diketopiperazine," J. Diabetes Sci. Technol., Sep. 2010, vol. 4(5), pp. 1164-1173 (Abstract Only Provided).

Prakash et al., "Synthesis and Biological Activity of Novel Neuroprotective Diketopiperazines," Bioorganic & Medicinal Chemistry, Sep. 2002, vol. 10(9), pp. 3043-3048.
Prasad et al., "Distribution and Characterization of Cyclo (His-Pro)-Like Immunoreactivity in Human Cerebrospinal Fluid," Biochem Biophys Res Commun, 1986, vol. 136(2), pp. 835-842 (Abstract Only Provided).
Prasad et al., "Distribution and Metabolism of Cyclo (His-Pro): A New Member of the Neuropeptide Family," Peptides, May-Jun. 1982, vol. 3(3), pp. 591-598 (Abstract Only Provided).
Prasad et al., "Increased cerebrospinal fluid cyclo(His-Pro) content in schizophrenia," Neuropeptides, Nov. 1991, vol. 20(3), pp. 187-190.
Prasad et al., "Isolation of cyclo(His-Pro)-like immunoreactivity from Human Urine and Demonstration of its Immunologic, Pharmacologic, and Physico-chemical Identity with the Synthetic Peptide," Biochemistry Int, 1990, vol. 21(3), pp. 425-434 (Abstract Only Provided).
Prasad et al., "Thermoregulation in rats: opposing effects of thyrotropin releasing hormone and its metabolite histidyl-proline diketopiperazine," Biochem Biophys Res. Commun., 1978, vol. 85(4), pp. 1582-2187.
Prasad, "Bioactive Cyclic Dipeptides," Peptides, 1995, vol. 16(1), pp. 151-164.
Purves et al. (Eds), Neuroscience, 2001, Sinauer Associates, Inc., 2nd Edition, pp. 75, 367, 400 and 403.
Purves et al., Life: the Science of Biology, 3rd Ed. (1992), p. 376.
Rainbow et al., "Distribution, survival and biological effects in mice of a behaviorally active, enzymatically stable peptide: pharmacokinetics of cyclo(Leu-Gly) and puromycin-induced amnesia," Pharmacol Biochem Behav, May 1979, vol. 10(5), pp. 787-793.
Rainger et al., "Endothelial-Borne Platelet-Activating Factor and Interleukin-8 Rapidly Immobilize Rolling Neutrophils," Am. J. Physiol., 272(Heart Circ. Physiol. 41):H114-H122 (1997).
Rainsford et al., "Effects of 5-Lipoxygenase Inhibitors on Interleukin Production by Human Synovial Tissues in Organ Culture: Comparison with Interleukin-1-Synthesis Inhibitors," J. Pharm. Pharmacol., 48:46-52 (1996).
Reubsaet et al., "Qualitative and Quantitative Aspects of the Degradation of Several Tripeptides Derived from the Antitumor Peptide Antagonist [Arg(6), D-Trp(7,9), MePhe(8)] Substance P[6-11]," J Pharm Biomed Anal 1999, 19(3-4):2.
Rinaldi et al. "Immunological markers in multiple sclerosis: tackiling the missing elements," Neurol. Sci., Dec. 2005, vol. 26 Suppl. 4, pp. S215-S217.
Rosenthal et al., "Effects of Arachidonic Acid and Cyclo (His-Pro) on Zinc Transport Across Small Intestine and Muscle Tissues," Life Sci, 2001, vol. 70(3), pp. 337-348 (Abstract Only Provided).
Roth et al., "Platelet-Activating Factor Exerts Mitogenic Activity and Stimulates Expression of Interleukin 6 and Interleukin 8 in Human Lung Fibroblasts via Binding to its Functional Receptor," J. Exp. Med., 1996, vol. 184, pp. 191-201.
Sakurada et al., "Antinociceptive activities of synthetic dipeptides in mice." J. Pharm. Pharmacol., 1982, vol. 34, pp. 750-751.
Sakuta et al., "Dual Regulatory Effects of Interferon-α, -β, and -γ on Interleukin-8 Gene Expression by Human Gingival Fibroblasts in Culture Upon Stimulation with Lipopolysaccharide from *Prevotella intermedia*, Interleukin-1α, or Tumor Necrosis Factor-α," J. Dent Res., 1998, vol. 77(8), pp. 1597-1605.
Samanta et al., "Crystal Structure of Human Plasma Platelet-activating Factor Acetylhydrolase," J. Biol. Chem., vol. 283(46), Nov. 14, 2008, pp. 31617-31624.
Sammes, "Naturally Occurring 2,5-Dioxopiperazines and Related Compounds," Fortschr. Chem. Org. Naturst., 1975, vol. 32, pp. 51-118.
Sano et al. "Process Research and Development of L-Alanyl-L-Glutamine, a Component of Parenteral Nutrition," Organic Process Research & Development, 2000, vol. 4, pp. 147-152.
Sato et al., "Comparison of the antiociceptive effect between the cyclic dipeptide cyclo[Tyr(Et)- homoarginine] and the linear dipeptide Boc-Tyr(Et)-homoarginine-Ome in rats.," Jpn J Pharmacol, Jan. 1984, vol. 34(1) (Abstract Only Provided).

(56) References Cited

OTHER PUBLICATIONS

Scharpe et al., "Peptide Truncation by Dipeptidyl Peptidase IV: A New Pathway for Drug Discovery," Verh K. Acad Geneeskd Belg. 2001, vol. 63(1), pp. 5-32 (Abstract Only Provided).

Schlingemann et al., "Role of vascular permeability factor/vascular endothelial growth factor in eye disease," Brit. J. Ophthalmology, vol. 81, 1997, pp. 501-512.

Sepetov et al., "Rearrangement, Racemization and Decomposition of Peptides in Aqueous Solution," Peptide Research, 1991, vol. 4(5), pp. 308-313 (Abstract Only Provided).

Seredenin et al. "Endogenous dipeptide cycloprolylglycine shows selective anxiolytic activity in animals with manifest fear reaction," Bull Exp Biol Med; Apr. 2002; vol. 1333(4) (Abstract Only Provided).

Shaw et al., "Future of early detection of lung cancer: the role of mouse models." Clin Cancer Res., Jul. 1; 11(13 Pt 2): 4999s-5003s, 2005.

Shimazaki et al., "Diketopiperazine Derivatives, a New Series of Platelet-Activating Factor Inhibitors," Chem. Pharm. Bull., 1987, vol. 35(8), pp. 3527-3530.

Shimazaki et al., "Diketopiperazines as a New Class of Platelet-Activating Factor Inhibitors," J. Med. Chem., 1987, vol. 30, pp. 1706-1709.

Shimazaki et al., "PAF Inhibitory Activity of Diketopiperazines: Structure-Activity Relationships," Lipids, 1991, vol. 26(12), pp. 1175-1178.

Shimi et al., "Isolation of Cairomycins A and C," Accession No. 1981:530895, retrieved from STN Oct. 6, 2010, p. 1.

Shimi et al., "Isolation of Cairomycins A and C," Antimicrobial Agents and Chemotherapy, Jun. 1981, vol. 19(6), pp. 941-944.

Shukla et al., "Role of Endogenous Cyclo(His-Pro) in Cold-Induced Hypothermia in the Desert Rat (*Mastomys natalensis*)," Peptides; 1994; 15(8):1471-4 (Abstract Only Provided).

Shutov et al., "[Diagnostic Significance of the type of in Vitro Interaction between Blood Lymphocytes and Serotonin in Multiple Sclerosis]," [Article in Russian], Zh Nevrol Psikhiatr Im S S Korsakova, 2002, vol. 102(4), pp. 35-38 (Abstract Only Provided).

Skates et al., "Molecular markers for early detection of renal carcinoma: investigative approach," Clin Cancer Res, Sep. 2004, vol. 10(18 Pt 2), pp. 6296S-6301S.

Smith et al., "Lesson 10, vol. 12—Asthma: Evolving Anti-Inflammatory Therapy," www.chestnet.org/education/pccu/vol12/ lesson10.html, pp. 1-8, printed Jul. 20, 2000.

Smith et al., "Recent developments in drug therapy for multiple sclerosis," Mult. Scler., 1999, vol. 5, pp. 110-120.

Smith et al., "Solid-phase synthesis of a library of piperazinediones and diazepinediones via Kaiser oxime resin." Bioorg. Med. Chem., 1998, vol. 8, pp. 2369-2374.

Sollid et al. "Is celiac disease an autoimmune disorder?" Current Opinion in Immunology, Dec. 2005, vol. 17, No. 6, pp. 595-600.

Sollis "Short and novel stereospecific synthesis of trisubstituted 2,5-diketopiperazines," J Org Chem, Jun. 2005, vol. 70(12), pp. 4735-4740 (Abstract Only Provided).

Song et al., "Body weight reduction in rats by oral treatment with zinc plus cyclo-(His-Pro)," Br. J. Pharmacol., Sep. 2009, vol. 158(2), pp. 442-450, Epub May 5, 2009 (Abstract Only Provided).

Song et al., "Synergistic Antidiabetic Activities of Zinc, Cyclo (His-Pro), and Arachidonic Acid," Metabolism 2001 50(1):53-59 (Abstract Only Provided).

Song et al., "Raw vegetable food containing high cyclo (his-pro) improved insulin sensitivity and body weight control," Metabolism, Nov. 2005, vol. 54(11), pp. 1480-1489 (Abstract Only Provided).

Stark et al., "Structures, sensory activity, and dose/response functions of 2,5-diketopiperazines in roasted cocoa nibs (*Theobroma cacao*)." J Agric Food Chem., Sep. 7, 2005, vol. 53(18), pp. 7222-7231 (Abstract Only Provided) PMID: 16131134.

Steiner et al., "Histidyl Proline Diketopiperazine (Cyclo [His-Pro]) in Eating Disorders," Neuropeptides, Oct. 1989, vol. 14(3), pp. 185-189 (Abstract Only Provided).

Strom et al., "*Lactobacillus plantarum* MiLAB 393 produces the antifungal cyclic dipeptides cyclo(L-Phe-L-Pro) and cyclo(L-Phe-trans-4-OH-L-Pro) and 3-phenyllactic acid.," Appl Environ Microbiol, Sep. 2002, vol. 68(9) (Abstract Only Provided).

Suzuki et al., "Effect of cyclic dipeptides containing histidine on pentobarbital narcosis," J. Pharm. Dyn., May 1981, vol. 4(5), pp. 377-379.

Takahara et al., "Detection in Human Serum by Radioimmunoassay of Histidyl-Proline Diketopiperazine, a Metabolite of Thyrotropin-Releasing Hormone," J Clinical Endocrinology, 1983, vol. 56(2), pp. 312-319 (Abstract Only Provided).

T Hart et al., "Evaluating the validity of animal models for research into therapies for immune-based disorders," DDT, 2004, vol. 9(12), pp. 517-524.

The Cytokine Handbook, edited by Thomson and Lotze, 4th edition, 2003 Academic Press, vol. I, London, UK, pp. 167-199, 456-474, 567-601.

The Cytokine Handbook, edited by Thomson and Lotze, 4th edition, 2003 Academic Press, vol. I, London, UK, pp. 169, 186, 187, 467, 570, 571, 838, 839, 1189-1193, 1197-1200.

The Cytokine Handbook, edited by Thomson and Lotze, 4th edition, 2003 Academic Press, vol. II, London, UK, pp. 838-860 and 1189-1211.

The Dictionary of Immunology, Fourth Edition, Edited by Herbert et al., 1995, pp. 51-52 and 69.

Unal et al., "Cyclo(Gly-Gln) inhibits the cardiorespiratory depression produced by beta-endorphin and morphine," Brain Research, 1997, vol. 747(1), pp. 52-59.

Vara et al., "PI3K/Akt signalling pathway and cancer," Cancer Treatment Reviews, 2004, vol. 30, pp. 193-204.

Varughese et al., "Crystal structure and conformation of cyclo-L-cystine," Int. J. Pept. Protein Res., vol. 18, Jul. 1981, pp. 88-102.

Vogel et al., "Disseminated tumor cells—Their detection and significance for prognosis of gastrointestinal and pancreatic carcinomas," Virchows Arch, 2001, vol. 439, pp. 109-117.

Walter et al., "Neurohypophyseal hormones, analogs, and fragments: their effect on puromycin-induced amnesia," Proc. Natl. Acad. Sci., Oct. 1975, vol. 72(10), pp. 4180-4184.

Walter et al., "The Cyclized C-Terminal Dipeptide of Arginine Vasopressin: Metabolic Stability and Antagonism of Puromycin-Induced Amnesia," Hormones and Behavior, 1982, vol. 16; p. 234-244.

Wang et al., "A facile pathway to synthesize diketopiperazine derivatives," Tetrahedron Lett, 2002, vol. 43, pp. 865-867.

Wang et al., "Novel inhibitors of plasminogen activator inhibitor-1: development of new templates from diketopiperazines," Bioorg Med Chem Lett, Sep. 2002, vol. 12(17), pp. 2367-2370 (Abstract Only Provided).

Weng et al., "Novel CCK-B receptor agonists: diketopiperazine analogues derived for CCK4 bioactive conformation," Regul Pept, Aug. 1996; vol. 65(1) (Abstract Only Provided).

Wennemers et al., "Diketopiperazine Receptors: A Novel Class of Highly Selective Receptors for Binding Small Peptides," Chem. Eur. J., 2001, vol. 7, No. 15, pp. 3342-3347.

Wilber et al., "Endogenous histidyl-proline diketopiperazine [cyclo (His-Pro)]: a potential satiety neuropeptide in normal and genetically obese rodents," Trans Assoc Am Physicians, 1983, vol. 96, pp. 131-136.

Wilber et al., "Histidyl-proline diketopiperazine: a potent and chronic appetite-inhibiting neuropeptide," Trans Assoc. Am Physicians, 1986, vol. 99, pp. 245-249.

Wilkes et al. "Patient Survival after Human Albumin Administration: A Meta-Analysis of Randomized, Controlled Trials." Annals of Internal Medicine, Aug. 2001, vol. 135, No. 3, pp. 149-164.

Wisniewski et al., "Relationship between serum cyclo (His-Pro) concentrations and the nutritional status of HIV-infected patients," South Med. J., Mar. 1994, vol. 87(3), pp. 348-351 (Abstract Only Provided).

Woehlecke et al., "Reversal of breast cancer resistance protein-mediated drug resistance by tryprostatin A.," Int J Cancer; Dec. 2003, vol. 107(5) (Abstract Only Provided).

(56) References Cited

OTHER PUBLICATIONS

Wolf et al., "Identification of Cyclo(His-Pro)-Like Immunoreactivity in Human Follicular Fluid: Correlation with Steroid and Peptide Hormones," J Soc Gynecol Investigation, 1994, vol. 1(3), pp. 220-224 (Abstract Only Provided).
Wretlind, "The Availability of the Isopropyl Ester of L- and D-Phenylalanine and 3,6-Dibenzyl-2,5-Diketopiperazine form Growth in Rats," Acta phys. Scandinav, May 1953, vol. 30, pp. 97-104.
Wyatt et al., "2,5-Diketopiperazines as potent and selective oxytocin antagonists 1: Identification, stereochemistry and initial SAR," Bioorg Med Chem Lett., May 16, 2005, vol. 15(10), pp. 2579-2582 (Abstract Only Provided) PMID: 15863320.
Yamada et al., "Abundance of Cyclo (His-Pro)-like Immunoreactivity in the Brain of TRH-Deficient Mice," Endocrinology, Jan. 1999, vol. 140(1), pp. 538-541 (Abstract Only Provided).
Yanagisawa et al., "The Subcellular and Organ Distribution and Natural Form of Histidyl-Proline Diketopiperazine in Rat Brain Determined by a Specific Radioimmunoassay," J Biol Chem, Nov. 10, 1980, vol. 255(21), pp. 10290-10294 (Abstract Only Provided).
Yang et al. "Increased hepatic platelet activating factor (PAF) and PAF receptors in carbon tetrachloride induced liver cirrhosis." Gut, Jan. 2004, vol. 53, No. 6, pp. 877-883.
Yi ES, "Hypersensitivity pneumonitis," Crit Rev Clin Lab Sci., Nov. 2002, vol. 39(6), pp. 581-629.
Yoshida et al., "PAF Inhibitors of Microbial Origin," Prog. Biochem. Pharmacol., 1988, vol. 22, pp. 68-80.
Youngblood et al., "Bovine Serum Albumin-GABA-His-Pro-NH2: an Immunogen for Production of Higher Affinity Antisera for TRH," J Neursci Methods, 1983, vol. 9(4), pp. 367-373 (Abstract Only Provided).
Zeng et al., "Synthesis of a small library of diketopiperazines as potential inhibitors of calpain," Bioorg Med Chem Lett, Jun. 2005, vol. 15(12), pp. 3034-3038.
International Search Report and Written Opinion for International (PCT) Patent Application No. PCT/US12/59455, mailed Dec. 6, 2012 9 pages.
Gomez et al., "Low-Dose Dopamine Agonist Administration Blocks Vascular Endothelial Growth Factor (VEGF)—Mediated Vascular Hyperpermeability without Altering VEGF Receptor 2-Dependent Luteal Angiogenesis in a Rat Ovarian Hyperstimulation Model," Endocrinology, 2006, vol. 147, No. 11, pp. 5400-5411.
"Diabetic Retinopathy—What you should know," National Institutes of Health, 2003, NIH Publication No. 06-2171, 24 pages.
Costa et al., "Aggregation of features of the metabolic syndrome is associated with increased prevalence of chronic complications in Type 2 diabetes," Diabetic Medicine, 2004, vol. 21, Iss. 3, 252-255.
De La Cruz et al, "Effect of WEB 2086-BS, an antagonist of platelet-activating factor receptors, on retinal vascularity in diabetic rats," European Journal of Pharmacology, 1998, vol. 360, Iss. 1, pp. 37-42.
Morely et al., "Histidyl-proline diketopiperazine decreases food intake in rats," Brain Research, 1981, vol. 210, Iss. 1-2, pp. 475-478.
Ramírez et al., "Platelet Activating Factor Modulates Microvascular Permeability through Nitric Oxide Synthesis," Microvascular Research, 1995, vol. 50, Iss. 2, pp. 223-234.
Brown et al., "Anti-VEGF Agents in the Treatment of Neovascular Age-related Macular Degeneration: Applying Clinical Trial Results to the Treatment of Everyday Patients," American Journal of Opthalmology, 2007, vol. 144, Iss. 4, pp. 627-637.
Hollyfield et al., "Oxidative damage-induced inflammation initiates age-related macular degeneration," Nature Medicine, 2008, vol. 14, No. 2, pp. 194-198.
Lewis et al., "Hydrogen Peroxide Stimulates the Synthesis of Platelet-activating Factor by Endothelium and Induces Endothelial Cell-dependent Neutrophil Adhesion," The Journal of Clinical Investigation, 1988, vol. 82, Iss. 6, pp. 2045-2055.
Ma et al., "Platelet-Activating Factor (PAF) Induces Corneal Neovascularization and Upregulates VEGF Expression in Endothelial Cells," Investigative Ophthalmology & Visual Science, 2004, vol. 45, No. 9, pp. 2915-2921.
Nicolson, "Metabolic syndrome and mitochondrial function: Molecular replacement and antioxidant supplements to prevent membrane peroxidation and restore mitochondrial function," Journal of Cellular Biochemistry, 2007, vol. 100, Iss. 6, pp. 1352-1369.
Otani et al., "Bone marrow-derived stem cells target retinal astrocytes and can promote or inhibit retinal angiogenesis," Nature Medicine, 2002, vol. 8, No. 9, pp. 1004-1010.
Chan, "Chapter 9: Transplant Rejection and Its Treatment," Atlas of Diseases of the Kidney, vol. 5, (Ed.Henrich et al.), Wiley-Blackwell, 1999, pp. 9.1-9.13.
Horwitz et al., "Piperazinedione plus total body irradiation: an alternative preparative regimen for allogeneic bone marrow transplantation in advanced phases of chronic myelogenous leukemia," Bone Marrow Transplantation, 1989, vol. 4, Iss. 1, pp. 101-105.
Zander et al., "Allogeneic bone marrow transplantation for acute leukemia refractory to induction chemotherapy," Cancer, 1985, vol. 56, Iss. 6, pp. 1374-1379.
International Preliminary Report on Patentability for International (PCT) Patent Application No. PCT/US12/59455 mailed Apr. 24, 2014, 8 pages.
Suguna et al., "Crystal structures of diketopiperazines containing α-aminoisobutyric acid: Cyclo(Aib-Aib) and cyclo(Aib-L-Ile)," Biopolymers, 1982, vol. 21, Iss. 9, pp. 1847-1855.
Official Action (English translation) for Chinese Patent Application No. 201280047779.1 dated Jan. 30, 2015, 6 pages.
Official Action for New Zealand Patent Application No. 623875 dated Dec. 15, 2014, 2 pages.
Albert et al., "ABT-491, a highly potent and selective PAF antagonist, inhibits nasal vascular permeability associated with experimental allergic rhinitis in Brown Norway rats," Inflamm. Res., 1997, Supplement 2, pp. S133-S134.
Berman et al., "Psoriasis," PubMed Health, reviewed Nov. 22, 2011, available at www.ncbi.nlm.nih.gov/pubmedhealth/PMH0001470/?report=printable.
Gossec et al., "Intra-articular treatments in osteoarthritis: from the symptomatic to the structure modifying," Annals of the Rheumatic Diseases, 2004, vol. 63, Iss. 5, pp. 478-482.
Lee et al., "Characterization of an Elastase Inhibitor Produced by *Streptomyces lavendulae* SMF11," Journal of Microbiology and Biotechnology, 2000, vol. 10, No. 1, pp. 81-85.
O'Connor et al., "Post-proline dipeptidyl-aminopeptidase from synaptosomal membranes of guinea-pig brain," European Journal of Biochemistry, 1986, vol. 154, Iss. 2, pp. 329-335.
Teitel et al., "Rheumatoid arthritis," PubMed Health, reviewed Feb. 2, 2012, available at www.ncbi.nlm.nih.gov/pubmedhealth/PMH0001467/?report=printable, 8 pages.
Teitel et al., "Scleroderma," PubMed Health, reviewed Feb. 2, 2012, available at www.ncbi.nlm.nih.gov/pubmedhealth/PMH0001465/?report=printable, 7 pages.
Teitel et al., "Systemic lupus erythematosus," PubMed Health, reviewed Feb. 2, 2012, available at www.ncbi.nlm.nih.gov/pubmedhealth/PMH0001471/?report=printable, 9 pages.
Zieve, "Multiple sclerosis," PubMed Health, reviewed Sep. 26, 2011, available at www.ncbi.nlm.nih.gov/pubmedhealth/PMH0001747/?report=printable, 10 pages.
Harada et al., "Essential involvement of interleukin-8 (IL-8) in acute inflammation," Journal of Leukocyte Biology, 1994, vol. 56, Iss. 5, pp. 559-564.
Lupia et al., "Role of tumor necrosis factor-a and platelet-activating factor in neoangiogenesis induced by synovial fluids of patients with rheumatoid arthritis," European Journal of Immunology, 1996, vol. 26, Iss. 8, pp. 1690-1694.
Shimonkevitz et al., "A Diketopiperazine Fragment of Human Serum Albumin Modulates T-Lymphocyte Cytokine Production Through Rap1," Journal of Trauma, Injury, Infection, and Critical Care, 2008, vol. 64, No. 1, pp. 35-41.
Notice of Allowance (with English translation) for Chinese Patent Application No. 201280047779.1 dated Mar. 6, 2015, 4 pages.
Extended European Search Report for European Patent Application No. 12839256.0 dated Feb. 20, 2015, 7 pages.
US 8,129,392, 03/2012, Bar-Or (withdrawn)

\* cited by examiner

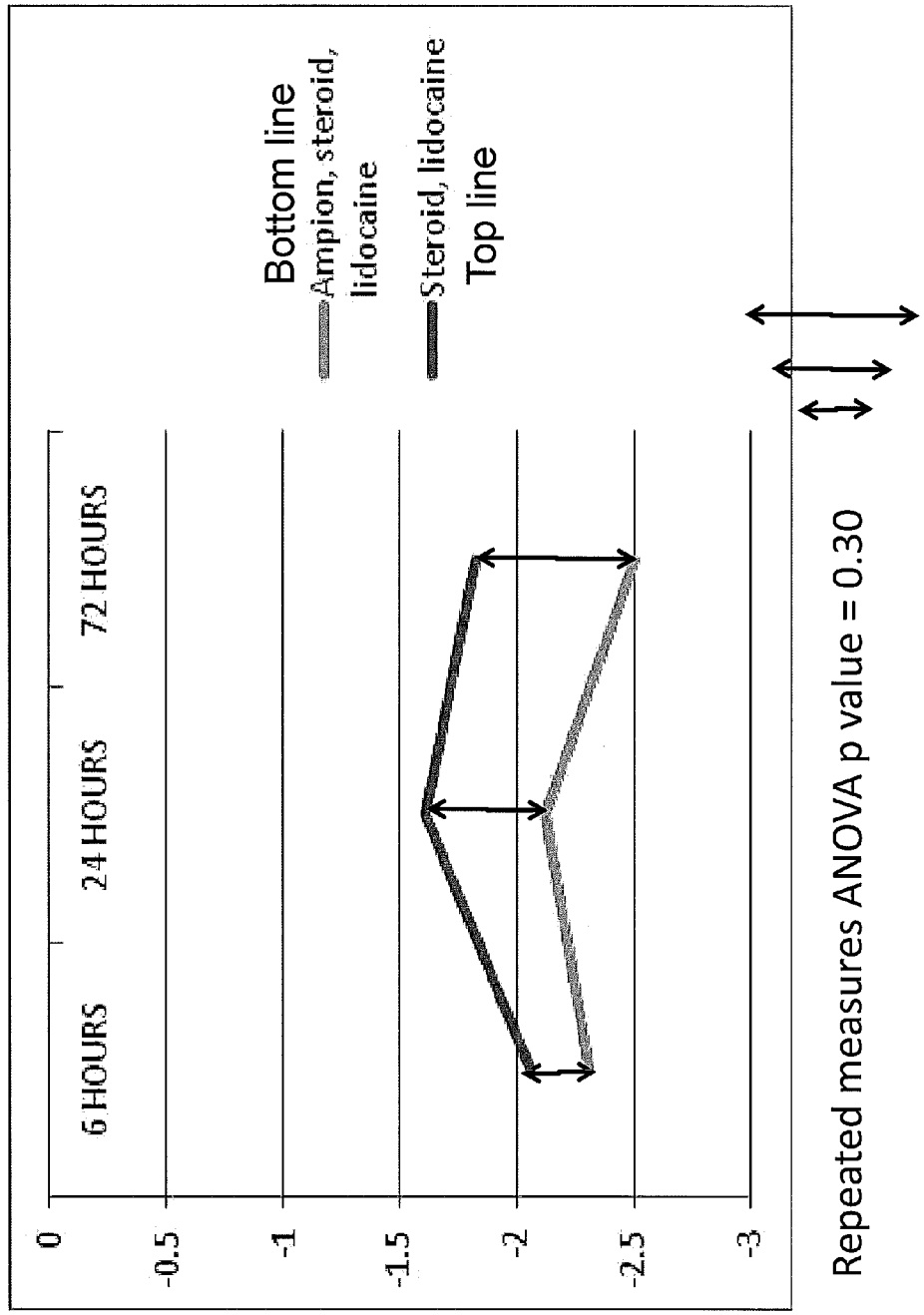

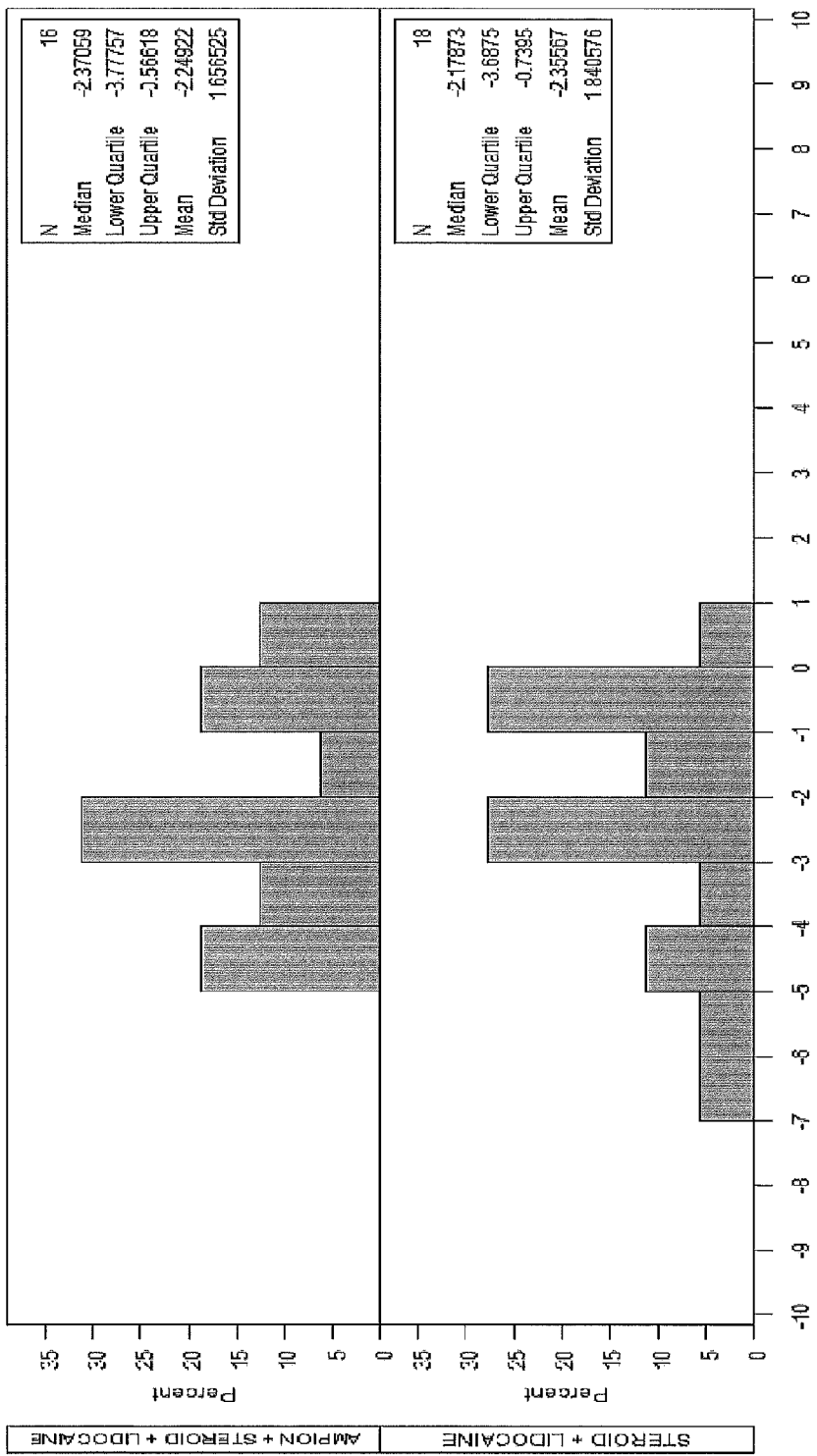

TREATMENT OF DEGENERATIVE JOINT DISEASE

CROSS-REFERENCE TO RELATED APPLICATIONS

This application is a continuation of PCT Application No. PCT/US2012/59455, having an international filing date of Oct. 10, 2012, which designated the United States. PCT Application No. PCT/US2012/59455 claims the benefit of priority under 35 U.S.C. §119(e) to U.S. Provisional Patent Application No. 61/545,474, filed Oct. 10, 2011 and U.S. Provisional Patent Application No. 61/561,221, filed Nov. 17, 2011. The entire disclosures of PCT/US2012/59455 and each U.S. Provisional Patent Applications Nos. 61/545,474 and 61/561,221 are incorporated herein by reference.

FIELD OF INVENTION

The invention relates to a method of treating a degenerative joint disease. The method comprises administering an effective amount of a pharmaceutical composition comprising a diketopiperazine with amino acid side chains of aspartic acid and alanine (DA-DKP). The invention also provides a pharmaceutical product comprising DA-DKP.

BACKGROUND

Osteoarthritis is the most common form of arthritis, affecting 25 to 35 million people in the U.S. Chronic pain and disability of osteoarthritis is initially caused by inflammatory responses in joint cartilage and bone that gradually worsens over time. Symptomatic osteoarthritis of the knee occurs in 10 to 13% of persons aged 60 and over. Knee osteoarthritis alone increases the risk of loss of mobility, such as needing assistance walking or climbing stairs, greater than for any other medical condition in people aged 65 and over.

Current drug treatment for osteoarthritis of the knee is limited to analgesics, nonsteroidal anti-inflammatory drugs (NSAIDs) and intra-articular steroid injections, all of which have significant limitations due to adverse effects. Despite these medical treatments, chronic knee osteoarthritis often causes progressive disability requiring total joint replacement. The increasing prevalence of osteoarthritis of the knee due to aging and obese populations suggests a growing clinical need for safe and effective local knee treatments that will delay and potentially eliminate the need for more extensive surgical treatments.

SUMMARY OF INVENTION

One embodiment of the invention relates to a method of treating a degenerative joint disease by administering to an animal in need thereof an effective amount of a pharmaceutical composition comprising DA-DKP. In one aspect, the degenerative joint disease is osteoarthritis.

In another aspect, the composition is administered no more frequently than once every six months, once every 5 months, once every 4 months, once every 3 months, or once every 2 months.

In yet another aspect, the composition can be administered by various administration routes. For example, the administration route may be by local administration, topical administration, or injection. In one aspect, administration by injection is by intra-articular injection. In yet another aspect, the composition administered by intra-articular injection is a composition having a concentration of DA-DKP from about 50 $\mu$M to about 350 $\mu$M.

In still another aspect, the composition further includes N-acetyl-tryptophan (NAT), caprylic acid, caprylate or combinations thereof. In yet another aspect, the concentration of NAT, caprylic acid, caprylate or combinations thereof in the composition may be about 4 mM to about 20 mM.

In yet other aspects of the method, the DA-DKP is in a composition prepared by removing albumin from a solution of a human serum albumin composition. For example, the step of removing can be by treating the human serum albumin composition by a separation method. Such separation methods can include ultrafiltration, sucrose gradient centrifugation, chromatography, salt precipitation, and sonication. In addition, the step of removing can be by passing the human serum albumin composition over an ultrafiltration membrane with a molecular weight cut off that retains the albumin, and the resulting filtrate contains the DA-DKP. In one aspect, the ultrafiltration membrane has a molecular weight cutoff of less than 50 kDa. In still another aspect, the ultrafiltration membrane has a molecular weight cut off less than 40 kDa, less than 30 kDa, less than 20 kDa, less than 10 kDa, less than 5 kDa or less than 3 kDa. In still another aspect, this composition further comprises NAT, caprylic acid, caprylate or combinations thereof. In yet another aspect, the concentration of NAT, caprylic acid, caprylate or combinations thereof in the composition may be about 4 mM to about 20 mM.

In another aspect, the method of the invention can further include administering a second drug. For example, the second drug can be an analgesic, an anti-inflammatory drug, or combinations thereof.

Another embodiment of the invention is a pharmaceutical product comprising a DA-DKP-containing composition formulated for administration by injection. In one aspect, the product is formulated for administration by intra-articular injection. In another aspect the DA-DKP is prepared by removing albumin from a solution of a human serum albumin composition. In one aspect, the step of removing the albumin can be by treating the human serum albumin composition by a separation method. For example, the separation method can be ultrafiltration, sucrose gradient centrifugation, chromatography, salt precipitation, or sonication. In addition, the step of removing can be by passing the human serum albumin composition over an ultrafiltration membrane with a molecular weight cut off that retains the albumin, and the resulting filtrate contains DA-DKP. In one aspect, the ultrafiltration membrane has a molecular weight cutoff of less than 50 kDa. In still another aspect, the ultrafiltration membrane has a molecular weight cut off less than 40 kDa, less than 30 kDa, less than 20 kDa, less than 10 kDa, less than 5 kDa or less than 3 kDa.

In yet another aspect, the DA-DKP of the pharmaceutical product that is administered by intra-articular injection is a composition having a concentration of DA-DKP from about 50 $\mu$M to about 350 $\mu$M.

In still another aspect, the product contains the DA-DKP composition that further contains NAT, caprylic acid, caprylate or combinations thereof. In yet another aspect, the concentration of NAT, caprylic acid, caprylate or combinations thereof in the product may be about 4 mM to about 20 mM.

In yet another aspect, the pharmaceutical product, further contains a pharmaceutically-acceptable carrier.

Another embodiment of the invention relates to a kit that includes a pharmaceutical product. In one aspect the product includes a DA-DKP-containing composition formulated for administration by injection. In still another aspect, the DA- DKP in the kit is prepared by removing albumin from a solution of a human serum albumin composition.

BRIEF DESCRIPTION OF THE DRAWINGS

FIG. 2 shows the mean change in pain NRS as described in FIG. 1 and includes a repeated measures analysis of variance (ANOVA).

FIG. 5B shows the absolute difference in WOMAC function subscores at 72 hours for the treatment described in FIG. 1.

DETAILED DESCRIPTION OF THE INVENTION

Figure 1:
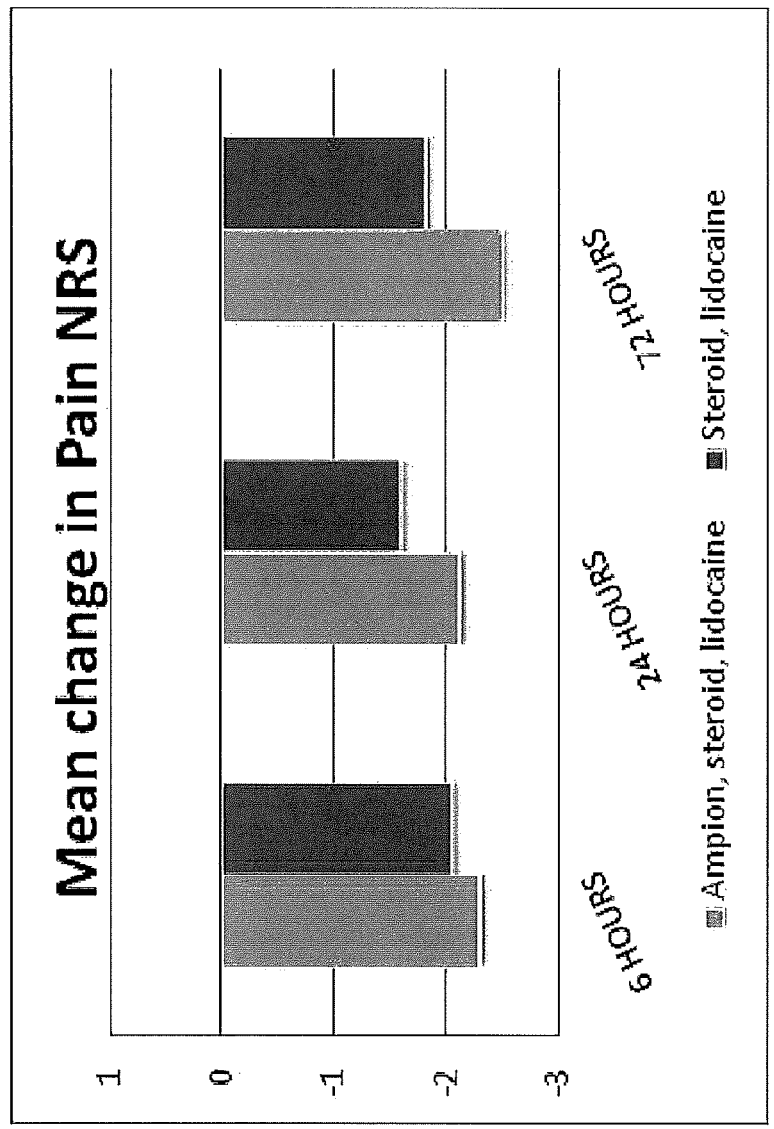
FIG. 1 shows the mean change in pain numerical rating scale (NRS) for subjects treated with a single 10 ml injection in one knee of Ampion™ (<5000 MW fraction) combined with a steroid (betamethasone)/lidocaine suspension or injected with a saline placebo combined with steroid (betamethasone)/lidocaine suspension. The scores were completed at 6 hours post-dose on Day 1, 24 hours post-dose on Day 2 and 72 hours post-dose on Day 4.

The present invention provides a method of treating a degenerative joint disease. The treatment comprises administering an effective amount of a pharmaceutical composition comprising aspartyl-alanyl diketopiperazine (DA-DKP) to an individual having a need thereof. DA-DKP has multiple anti-inflammatory and immune modulating effects including inhibition of multiple pro-inflammatory cytokines, chemokines and signaling molecules at the transcription level, inhibition of the migration and adhesion of T-cells and monocytes, activity at the G-coupled protein receptor level, activity on actin-dependent cytoskeletal events, reduction in vascular permeability and inhibition of inflammation induced by platelet activating factor. As described in more detail below, the effects of DA-DKP on degenerative joint disease have been found to be unexpectedly long lasting and in some studies were found to increase in time as compared to the use of steroids.

The invention also provides for a pharmaceutical product comprising a DA-DKP composition. The DA-DKP of the product may be prepared by removing albumin from a solution of human serum albumin.

The invention also provides for kit comprising a DA-DKP composition formulated for administration by injection.

A degenerative joint disease is a gradual deterioration of the articular cartilage that covers joints. A degenerative joint disease (osteoarthritis) is a noninfectious progressive disorder of the weightbearing joints. The normal articular joint cartilage is smooth, white, and translucent. It is composed of cartilage cells (chondrocytes) imbedded in a sponge-like matrix made of collagen, protein polysaccharides, and water. With early primary arthritis, the cartilage becomes yellow and opaque with localized areas of softening and roughening of the surfaces. As degeneration progresses, the soft areas become cracked and worn, exposing bone under the cartilage. The bone then begins to remodel and increase in density while any remaining cartilage begins to fray. Eventually, osteophytes (spurs of new bone) covered by cartilage form at the edge of the joint. As mechanical wear increases, the cartilage needs repairing. The cartilage cells are unable to produce enough of the sponge-like matrix and therefore the damaged cartilage cannot repair itself. The cartilage has no blood supply to enhance healing. The majority of degenerative joint disease is the result of mechanical instabilities or aging changes within the joint. This includes old age degenerative arthritis and, in younger individuals, may be the result of injuries, bruises, abnormal joint configuration (i.e. hip dysplasia), or mechanical wear from anterior cruciate ligament rupture, patellar luxation, or osteochondritis dissecans, for example. Degenerative joint disease can occur at any joint in the body, including without limitation, knee, hip, shoulder, hand and spine.

Conventional pharmaceutical therapies for degenerative joint disease include acetaminophen, nonsteroidal anti-inflammatory drugs (NSAIDS), narcotics, and corticosteroids.

"Treat" is used herein to mean to reduce (wholly or partially) the symptoms, duration or severity of a disease.

The pharmaceutical composition comprising DA-DKP of the invention is administered to an animal in need of treatment. Preferably, the animal is a mammal, such as a rabbit, goat, dog, cat, horse or human. Effective dosage amounts may vary with the severity of the disease or condition, the route(s) of administration, the duration of the treatment, the identify of any other drugs being administered to the animal, the age, size and species of the animal, and like factors known in the medical and veterinary arts.

Because the treatment of the present invention provides a long-lasting effect on the symptoms of degenerative joint disease, one aspect of the present invention is that the composition comprising DA-DKP may be administered to an animal at longer time intervals than would be expected for conventional therapies. For example, the present composition can be administered no more frequently than once every six month, once every five months, once every four months, once every three months, once every two months, once every month, once every four weeks, once every three weeks, once every two weeks or once every week.

The composition of the present invention comprising DA-DKP may be administered to an animal patient for therapy by any suitable route of administration, including locally, parenterally (e.g., injection, intra-articular injection, intravenously, intraspinally, intraperitoneally, subcutaneously, or intramuscularly), transdermally, and topically. A preferred route of administration is intra-articular injection.

The composition of the present invention may be a pharmaceutical solution having a DA-DKP concentration range with a lower endpoint of about 10 µM, about 20 µM, about 30 µM, about 40 µM, about 50 µM, about 60 µM, about 70 µM, about 80 µM, about 90 µM, about 100 µM, about 110 µM, about 120 µM, about 130 µM, about 140 µM, about 150 µM, about 160 µM, about 170 µM, about 180 µM, about 190 µM, about 200 µM, about 210 µM, about 220 µM, about 230 µM, about 240 µM, about 240, about 250 µM, about 260 µM, about 270 µM, about 280 µM, about 290 µM, about 300 µM, about 310, about 320 µM, about 330 µM, about 340 µM, about 350 µM, about 360 µM, about 370 µM, about 380 µM, about 390 µM, or about 400 µM. The composition of the present invention may be a pharmaceutical solution having a DA-DKP concentration range with an upper endpoint of about 600 µM, about 580 µM, about 570 µM, about 560 µM, about 550 µM, about 540 µM, about 530 µM, about 520 µM, about 510 µM, about 500 µM, about 490 µM, about 480 µM, about 470 µM, about 460 µM, about 450 µM, about 440 µM, about 430 µM, about 420 µM, about 410 µM, about 400 µM, about 390 µM, about 380 µM, about 370 µM, about 360 µM, about 350, about 340 µM, about 330 µM, about 320 µM, about 310 µM, about 300 µM, about 290 µM, about 280, about 270 µM, about 260 µM, about 250 µM, about 240 µM, about 230 µM, about 220 µM, about 210 µM, or about 200 µM.

An effective amount of DA-DKP in the composition of the present invention for treating a degenerative joint disease or condition can be a range with a lower endpoint of about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 425 µg, about 450 µg, about 475 µg or about 500 µg. In addition, an effective amount of DA-DKP in the composition of the present invention for treating a degenerative joint disease or condition can be a range with upper endpoint of about 500 µg, about 490 µg, about 480 µg, about 470 µg, about 460 µg, about 450 µg, about 440 µg, about 430 µg, about 420 µg, about 410 µg, about 400 µg, about 390 µg, about 380 µg, about 370 µg, about 360 µg, about 350 µg, about 340 µg, about 330 µg, about 320 µg, about 310 µg, about 300 µg, about 290 µg, about 280 µg, about 270 µg, about 260 µg, about 250 µg, about 240 µg, about 230 µg, about 220 µg, about 210 µg, about 200 µg, about 190 µg, about 180 µg, about 170 µg, about 160 µg, about 150 µg, about 140 µg, about 130 µg, about 120 µg, about 110 µg, about 100 µg, about 90 µg, about 80 µg, about 70 µg, about 60 µg, about 50 µg, about 40 µg, about 30 µg, or about 20 µg.

Dosage forms for the topical or transdermal administration of compounds of the invention include powders, sprays, ointments, pastes, creams, lotions, gels, solutions, patches, and drops. The active ingredient may be mixed under sterile conditions with a pharmaceutically-acceptable carrier, and with any buffers, or propellants which may be required.

The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Kits comprising the pharmaceutical products of the present invention are also provided. The kits can comprise a DA-DKP composition formulated for administration by injection. The DA-DKP can be prepared as described herein, such as by removing albumin from a solution of a human albumin composition. The kits may contain unit-dose or multi-dose sealed containers, for example, ampoules and vials, and may be stored in a lyophilized condition requiring only the addition of the sterile liquid carrier, for example water for injection, immediately prior to use. The kits may also be stored in a condition, wherein the contents are ready for direct use or injection.

While it is possible for a compound of the present invention to be administered alone, it is preferable to administer the compound as a pharmaceutical formulation (composition). The pharmaceutical compositions of the invention comprise a compound or compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., Remington's Pharmaceutical Sciences.

The composition of the present invention may further comprise N-acetyl-tryptophan (NAT), caprylic acid, caprylate or combinations thereof. Preferably, the composition may comprise NAT. Compositions of the present invention having NAT, caprylic acid, caprylate or combinations thereof may be a pharmaceutical composition having a NAT, caprylic acid, caprylate or combinations thereof concentration range with a lower endpoint of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM. In addition, compositions of the present invention having NAT, caprylic acid, caprylate or combinations thereof may be a pharmaceutical composition having a NAT, caprylic acid, caprylate or combinations thereof concentration range with an upper endpoint of about 40 mM, about 39 mM, about 38 mM, about 37 mM, about 36 mM, about 35 mM, about 34 mM, about 33 mM, about 32 mM, about 31 mM, about 30 mM, about 29 mM, about 28 mM, about 27 mM, about 26 mM, about 25 mM, about 24 mM, about 23 mM, about 22, or about 21 mM. Preferably, the concentration range is about 4 mM to about 20 mM.

In addition, the composition of the present invention may also comprise a second drug such as an analgesic (such as lidocaine or paracetoamol), an anti-inflammatory (such as bethamethasone, non-steroid anti-inflammatory drugs (NSAIDs), acetaminophen, ibuprofen, naproxen), and/or other suitable drugs.

Methods of making diketopiperazines, such as DA-DKP, are well known in the art, and these methods may be employed to synthesize the diketopiperazines of the invention. See, e.g., U.S. Pat. Nos. 4,694,081, 5,817,751, 5,990, 112, 5,932,579 and 6,555,543, US Patent Application Publication Number 2004/0024180, PCT applications WO 96/00391 and WO 97/48685, and Smith et al., Bioorg. Med. Chem. Letters, 8, 2369-2374 (1998), the complete disclosures of which are incorporated herein by reference.

For instance, diketopiperazines, such as DA-DKP, can be prepared by first synthesizing dipeptides. The dipeptides can be synthesized by methods well known in the art using L-amino acids, D-amino acids or a combination of D- and L-amino acids. Preferred are solid-phase peptide synthetic methods. Of course, dipeptides are also available commercially from numerous sources, including DMI Synthesis Ltd., Cardiff, UK (custom synthesis), Sigma-Aldrich, St. Louis, Mo. (primarily custom synthesis), Phoenix Pharmaceuticals, Inc., Belmont, Calif. (custom synthesis), Fisher Scientific (custom synthesis) and Advanced ChemTech, Louisville, Ky.

Once the dipeptide is synthesized or purchased, it is cyclized to form a diketopiperazine. This can be accomplished by a variety of techniques. For example, U.S. Patent Application Publication Number 2004/0024180 describes a method of cyclizing dipeptides. Briefly, the dipeptide is heated in an organic solvent while removing water by distillation. Preferably, the organic solvent is a low-boiling azeotrope with water, such as acetonitrile, allyl alcohol, benzene, benzyl alcohol, n-butanol, 2-butanol, t-butanol, acetic acid butylester, carbon tetrachloride, chlorobenzene chloroform, cyclohexane, 1,2-dichlorethane, diethylacetal, dimethylacetal, acetic acid ethylester, heptane, methylisobutylketone, 3-pentanol, toluene and xylene. The temperature depends on the reaction speed at which the cyclization takes place and on the type of azeotroping agent used. The reaction is preferably carried out at 50-200° C., more preferably 80-150° C. The pH range in which cyclization takes place can be easily determine by the person skilled in the art. It will advantageously be 2-9, preferably 3-7.

When one or both of the amino acids of the dipeptide has, or is derivatized to have, a carboxyl group on its side chain (e.g., aspartic acid or glutamic acid), the dipeptide is preferably cyclized as described in U.S. Pat. No. 6,555,543. Briefly, the dipeptide, with the side-chain carboxyl still protected, is heated under neutral conditions. Typically, the dipeptide will be heated at from about 80° C. to about 180° C., preferably at about 120° C. The solvent will be a neutral solvent. For instance, the solvent may comprise an alcohol (such as butanol, methanol, ethanol, and higher alcohols, but not phenol) and an azeotropic co-solvent (such as toluene, benzene, or xylene). Preferably, the alcohol is butan-2-ol, and the azeotropic co-solvent is toluene. The heating is continued until the reaction is complete, and such times can be determined empirically. Typically, the dipeptide will be cyclized by refluxing it for about 8-24 hours, preferably about 18 hours. Finally, the protecting group is removed from the diketopiperazine. In doing so, the use of strong acids (mineral acids, such as sulfuric or hydrochloric acids), strong bases (alkaline bases, such as potassium hydroxide or sodium hydroxide), and strong reducing agents (e.g., lithium aluminum hydride) should be avoided, in order to maintain the chirality of the final compound.

Dipeptides made on solid phase resins can be cyclized and released from the resin in one step. See, e.g., U.S. Pat. No. 5,817,751. For instance, the resin having an N-alkylated dipeptide attached is suspended in toluene or toluene/ethanol in the presence of acetic acid (e.g., 1%) or triethylamine (e.g., 4%). Typically, basic cyclization conditions are preferred for their faster cyclization times.

Other methods of cyclizing dipeptides and of making diketopiperazines are known in the art and can be used in the preparation of diketopiperazines useful in the practice of the invention. See, e.g., those references listed above. In addition, many diketopiperazines suitable for use in the present invention can be made as described below from proteins and peptides. Further, diketopiperazines for use in the practice of the invention can be obtained commercially from, e.g., DMI Synthesis Ltd., Cardiff, UK (custom synthesis).

The DA-DKP composition and/or products of the present invention can be prepared from solutions containing DA-DKP, including from the commercially-available pharmaceutical compositions comprising albumin, such as human serum albumin, by well known methods, such as ultrafiltration, chromatography (size-exclusion chromatography (e.g., Centricon filtration), affinity chromatography (e.g., using a column of beads having attached thereto an antibody or antibodies directed to the desired diketopiperazine(s) or an antibody or antibodies directed to the truncated protein or peptide), anion exchange or cation exchange), sucrose gradient centrifugation, chromatography, salt precipitation, or sonication, that will remove some or all of the albumin in the solution. The resultant DA-DKP-containing composition and/or product can be used and incorporated into pharmaceutical compositions as described above.

Using an ultrafilration separation method, a human serum albumin composition can be passed over an ultrafiltration membrane having a molecular weight cut-off that retains the albumin while the DA-DKP passes into the resulting filtrate or fraction. This filtrate may comprise components having molecular weights less than about 50 kDA, less than about 40 kDa, less than 30 kDa, less than about 20 kDa, less than about 10 kDa, less than about 5 kDa, less than about 3 kDa. Preferably, the filtrate comprises components having molecular weights less than about 5 Da (also referred to as "<5000 MW"). This <5000 MW fraction or filtrate contains DA-DKP which is formed after the dipeptide aspartate-alanine is cleaved from albumin and subsequently cyclized into the diketopiperazine.

Physiologically-acceptable salts of the DA-DKP of the invention may also be used in the practice of the invention. Physiologically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid.

As used herein, "a" or "an" means one or more.

As used herein, "comprises" and "comprising" include within their scope all narrower terms, such as "consisting essentially of" and "consisting of" as alternative embodiments of the present invention characterized herein by "comprises" or "comprising". In regard to use of "consisting essentially of", this phrase limits the scope of a claim to the specified steps and materials and those that do not materially affect the basic and novel characteristics of the invention disclosed herein.

Additional objects, advantages and novel features of the present invention will become apparent to those skilled in the art by consideration of the following non-limiting examples. The following experimental results are provided for purposes of illustration and are not intended to limit the scope of the invention.

EXAMPLES

Example 1

A clinical trial was performed to investigate the effect of intra-articular knee injection of a <5000 MW fraction of human serum albumin (also referred to herein as "Ampion™") for improving joint function and reducing the pain of osteoarthritis of the knee. A randomized, placebo-controlled, double-blind, parallel study with 60 evaluable subjects was chosen as the appropriate design to estimate the treatment effect and safety of the <5000 MW Fraction when it was injected into the study knee.

Primary Objective:

To investigate the reduction of pain in subjects with knee osteoarthritis of a single 10 ml intra-articular injection containing the <5000 MW Fraction combined with lidocaine/betamethasone suspension compared with the <5000 MW Fraction combined with betamethasone suspension or compared with a saline placebo combined with lidocaine/betamethasone suspension.

Secondary Objectives:

To investigate joint function and pain in subjects with knee osteoarthritis, as assessed by the Western Ontario McMaster University Osteoarthritis (WOMAC) Index (Bellamy et al., "Validation study of WOMAC: a health status instrument for measuring clinically important patient relevant outcomes to antirheumatic drug therapy in patients with osteoarthritis of the hip or knee." *J Rheumatology* 1988; 15:1833-1840) of a single intra-articular injection of the <5000 MW Fraction combined with lidocaine/betamethasone suspension compared with the <5000 MW Fraction combined with betamethasone suspension or compared with a saline placebo combined with lidocaine/betamethasone suspension.

To investigate the requirement for rescue medications in subjects with knee osteoarthritis, after a single intra-articular injection of the <5000 MW Fraction combined with lidocaine/betamethasone suspension compared with the <5000 MW Fraction combined with betamethasone suspension or compared with a saline placebo combined with lidocaine/betamethasone suspension.

To investigate the effect on the range of motion in subjects with knee osteoarthritis and limited range of motion in the study knee due to pain and inflammation, after a single intra-articular injection of the <5000 MW Fraction combined with lidocaine/betamethasone suspension compared with the <5000 MW Fraction combined with betamethasone suspension or compared with a saline placebo combined with lidocaine/betamethasone suspension.

To compare safety and tolerability between treatments as assessed by reported adverse events in the study population.

Description of the Protocol

This study was a randomized, placebo-controlled, double-blind, parallel study designed to evaluate the effect of intra-articular knee injection of the <5000 MW Fraction in male or female subjects ≥40 years old with symptomatic primary knee osteoarthritis for 6 months preceding screening. The study consisted of a 3 week screening period and a 4 day study participation period. Each subject was randomized to receive a single 10 mL knee injection of one of the following:
- the <5000 MW Fraction combined with lidocaine/betamethasone suspension
- the <5000 MW Fraction combined with betamethasone suspension
- saline placebo combined with lidocaine/betamethasone suspension Subjects were allowed to leave the clinic following a satisfactory post-dose review by the investigator. Follow-up assessments were performed at 6 hours, 24 hours (Day 2) and 72 hours (Day 4) post-injection. These assessments were conducted at the clinic or externally (e.g. home visit), at the discretion of the investigator.

Duration of Study Participation:

Screening: Between Day—21 and Day—1.

Treatment Period: A single injection in the study knee with clinical follow-up over 72 hours, including dosing on Day 1 and follow-up visits on Day 2 and Day 4.

The total duration of study participation was approximately 72 hours for each subject, with a screening interval of up to 21 days.

Study Treatments

Each subject received a single 10 mL injection in one knee of one of the following treatments:
  <5000 MW Fraction combined with lidocaine/betamethasone suspension
  <5000 MW Fraction combined with betamethasone suspension
  saline placebo combined with lidocaine/betamethasone suspension Study Population The study population was 60 patients, male or female, 40-85 years old, fully ambulatory, with symptomatic primary knee osteoarthritis for more than 6 months prior to screening with Kellgren Lawrence Grade II or III.

Description of Investigational Product

Sterile 2 mL <5000 MW Fraction in rubber stopper storage vials was prepared by Sypharma Pty Ltd., Dandenong, Victoria, Australia. The <5000 MW Fraction was combined with either lidocaine/betamethasone suspension or betamethasone suspension in a blinded fashion prior to injection. Saline placebo combined with lidocaine/betamethasone suspension was administered as a third treatment. See Table 1

TABLE 1

| Investigational Product Components: | | | |
|---|---|---|---|
| <5000 MW Fraction | Bethamethasone | Lidocaine | Saline |
| Treatment A | 4 mL | 2 mL | 4 mL | Nil |
| Treatment B | 4 mL | 2 mL | Nil | 4 mL |
| Treatment C | Nil | 2 mL | 4 mL | 4 mL |

A single 10 mL injection of study drug combined with lidocaine/betamethasone suspension or combined with betamethasone suspension was injected into the knee joint space under sterile prep conditions using an 18-21 gauge needle.

Study drug was stored at room temperature (59°-77° F. or 15°-25° C.) in a secure area with restricted access.

Randomization and Allocation to Study Treatment

Subjects were allocated to a sequentially numbered treatment in accordance with the randomization schedule following confirmation of eligibility at pre-dose. Each subject was assigned to one of the three treatments, i.e. active <5000 MW Fraction (either combined with lidocaine/betamethasone or betamethasone suspension) or saline placebo combined with lidocaine/betamethasone. The allocation of treatment was performed using a block randomization algorithm.

If both knees were osteoarthritic, then at Screening the investigator selected one knee to be the study knee, being the knee that best satisfied the requirements for the study. At the time of dose administration, the study knee received investigational product in accordance with the randomization schedule. The other knee received normal standard of care.

Efficacy Measures

The range of motion in the study knee was examined by the investigator or nominee for subjects with limited range of motion due to pain and inflammation at pre-dose, 24 and 72 hours post-dose and the global pain assessment (pain numerical rating scale) was performed at pre-dose, 6, 24 and 72 hours post-dose and Western Ontario McMaster University Osteoarthritis (WOMAC) Index 3.1 was completed by subjects at pre-dose, 24 and 72 hours post-dose.

The pain numerical rating scale (NRS) in the study knee was completed at pre-dose, 6 hours post-dose on Day 1, 24 hours post-dose on Day 2 and 72 hours post-dose on Day 4. The pain numerical rating scale was completed prior to WOMAC if the pain scale and WOMAC occur at the same time. The pain NRS is a numerical rating of 0-10, with 0 being no pain, 5 being moderate pain and 10 being worst possible pain.

The range of motion (degrees of flexion and extension) in the study knee was examined by the investigator or nominee for subjects with limited range of motion due to pain and inflammation not by osteophyte growth, at baseline, 24 hours post-dose on Day 2 and 72 hours post-dose on Day 4.

WOMAC Index 3.1 was completed by subjects within 1 hour prior to injection, 24 hours post-dose on Day 2 and 72 hours post-dose on Day 4. The WOMAC Index assesses joint function and pain in subjects with hip or knee osteoarthritis. It measures 24 parameters (questions) with each parameter (question) being rated by the subject on a scale of 1-10. There are three subscores: pain (5 questions); stiffness (2 questions); and function (17 questions).

Figure 3A:
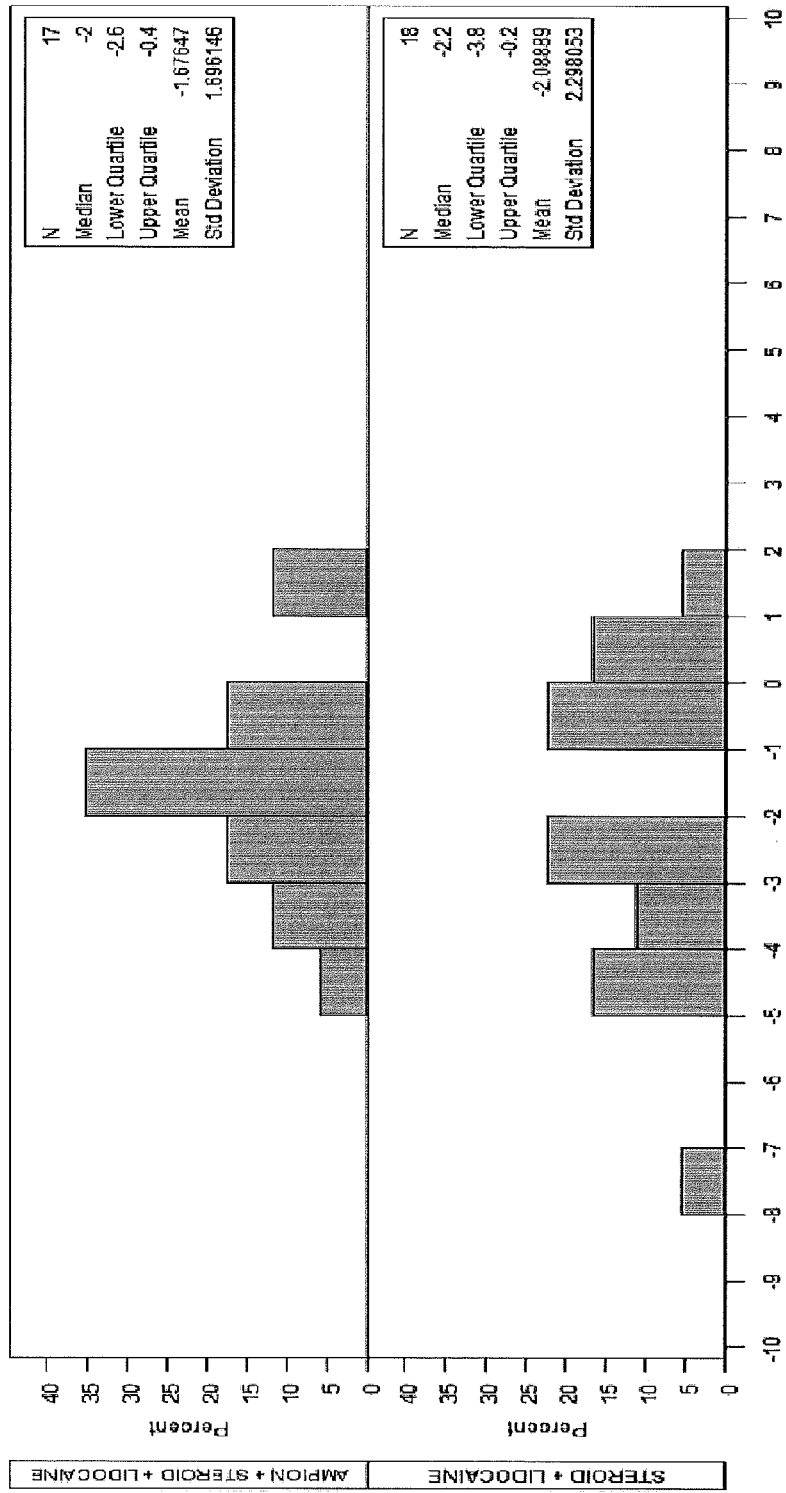
FIG. 3A shows the absolute difference in WOMAC (Western Ontario McMaster University Osteoarthritis Index 3.1) pain subscores at 24 hours for the treatment described in FIG. 1.
Figure 3B:
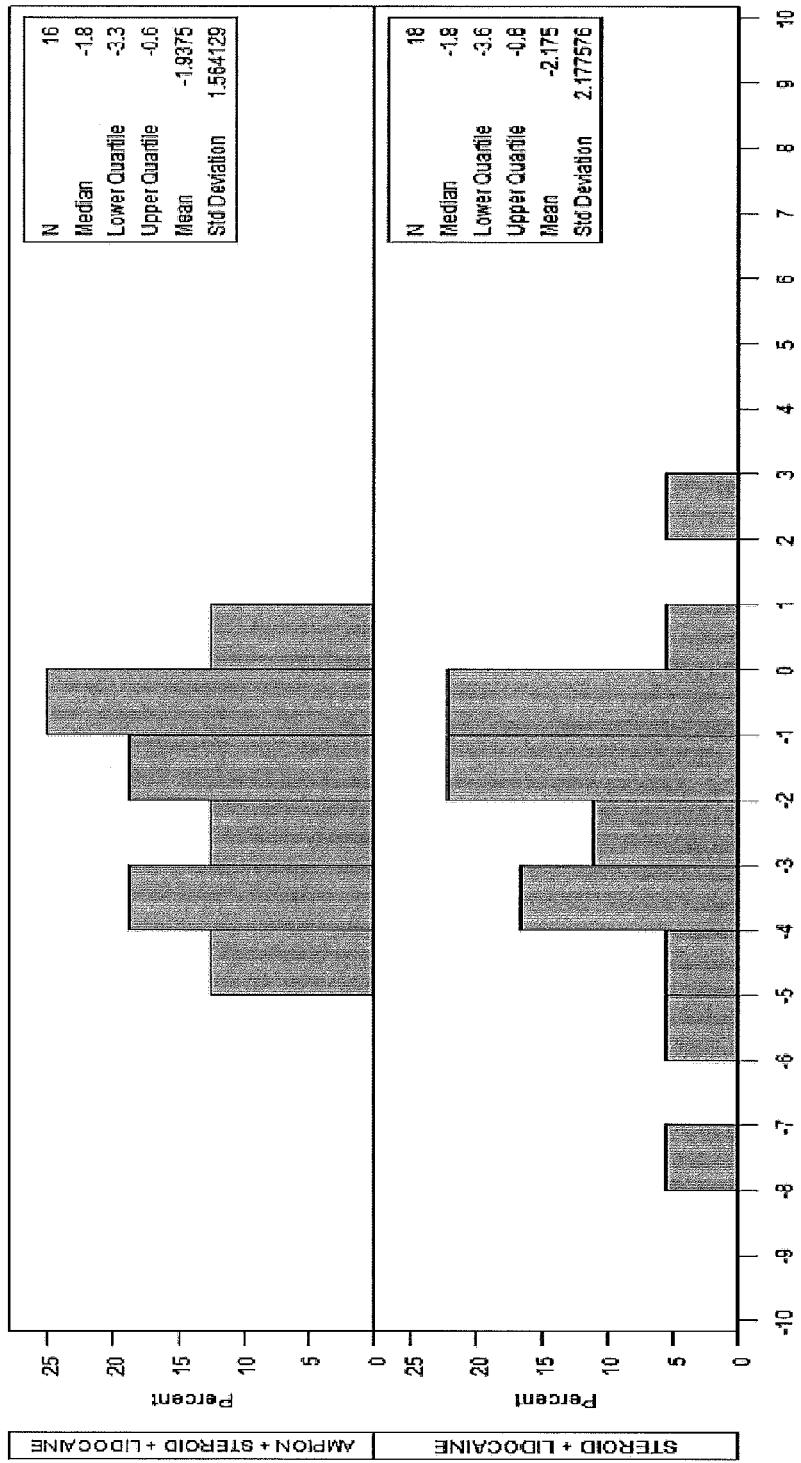
FIG. 3B shows the absolute difference in WOMAC pain subscores at 72 hours for the treatment described in FIG. 1.
Figure 4A:
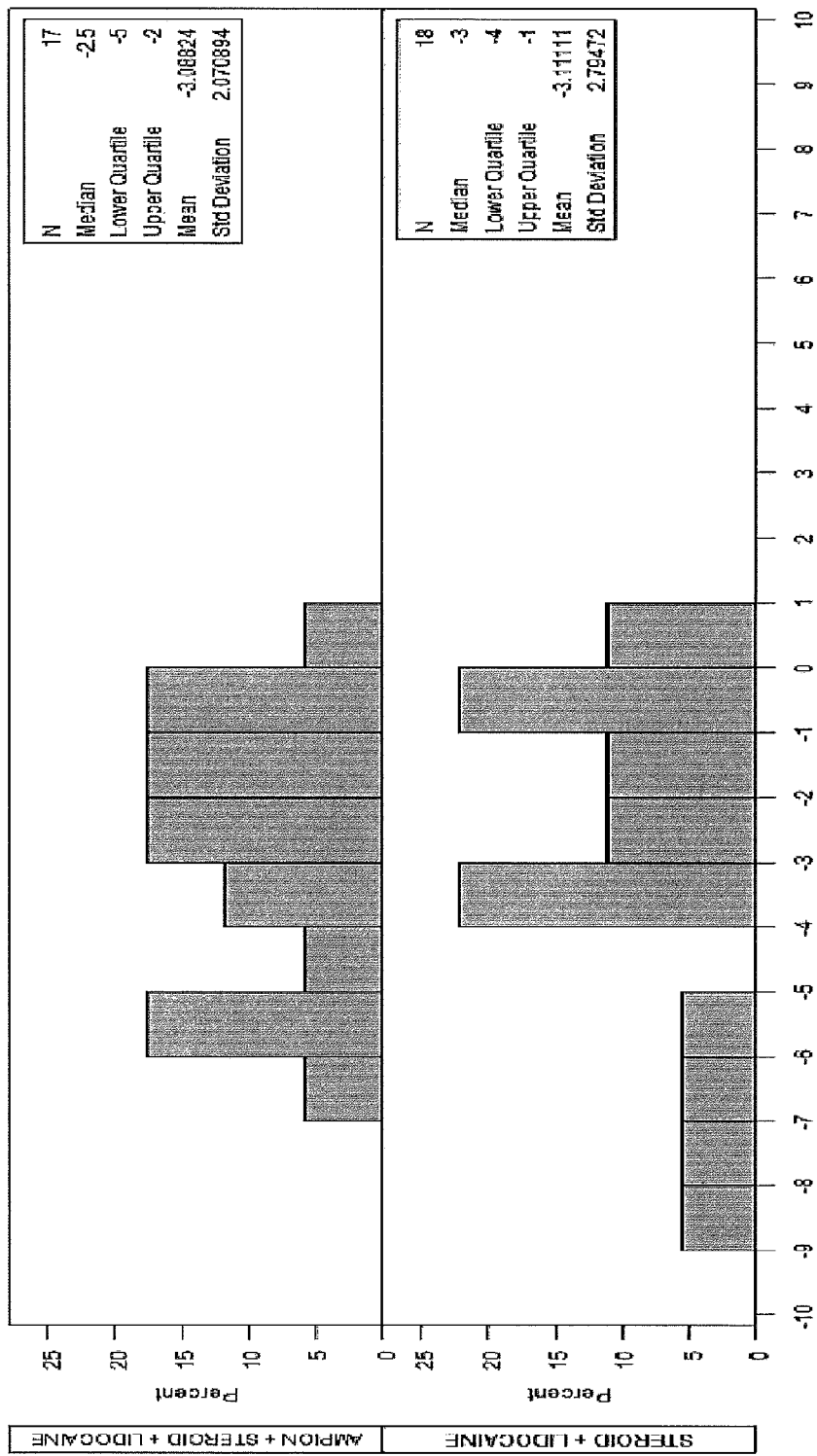
FIG. 4A shows the absolute difference in WOMAC stiffness subscores at 24 hours for the treatment described in FIG. 1.
Figure 4B:
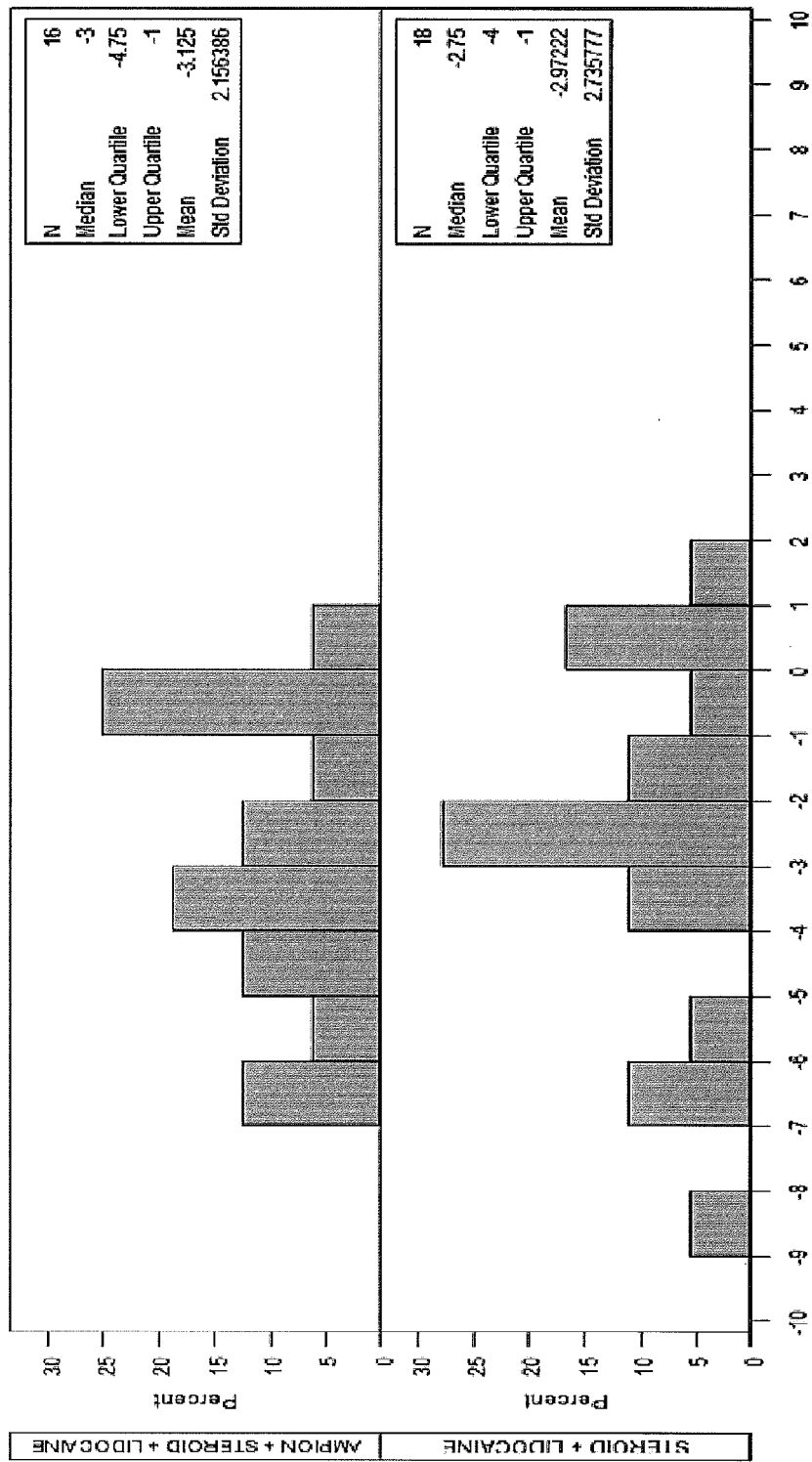
FIG. 4B shows the absolute difference in WOMAC stiffness subscores at 72 hours for the treatment described in FIG. 1.
Figure 5A:
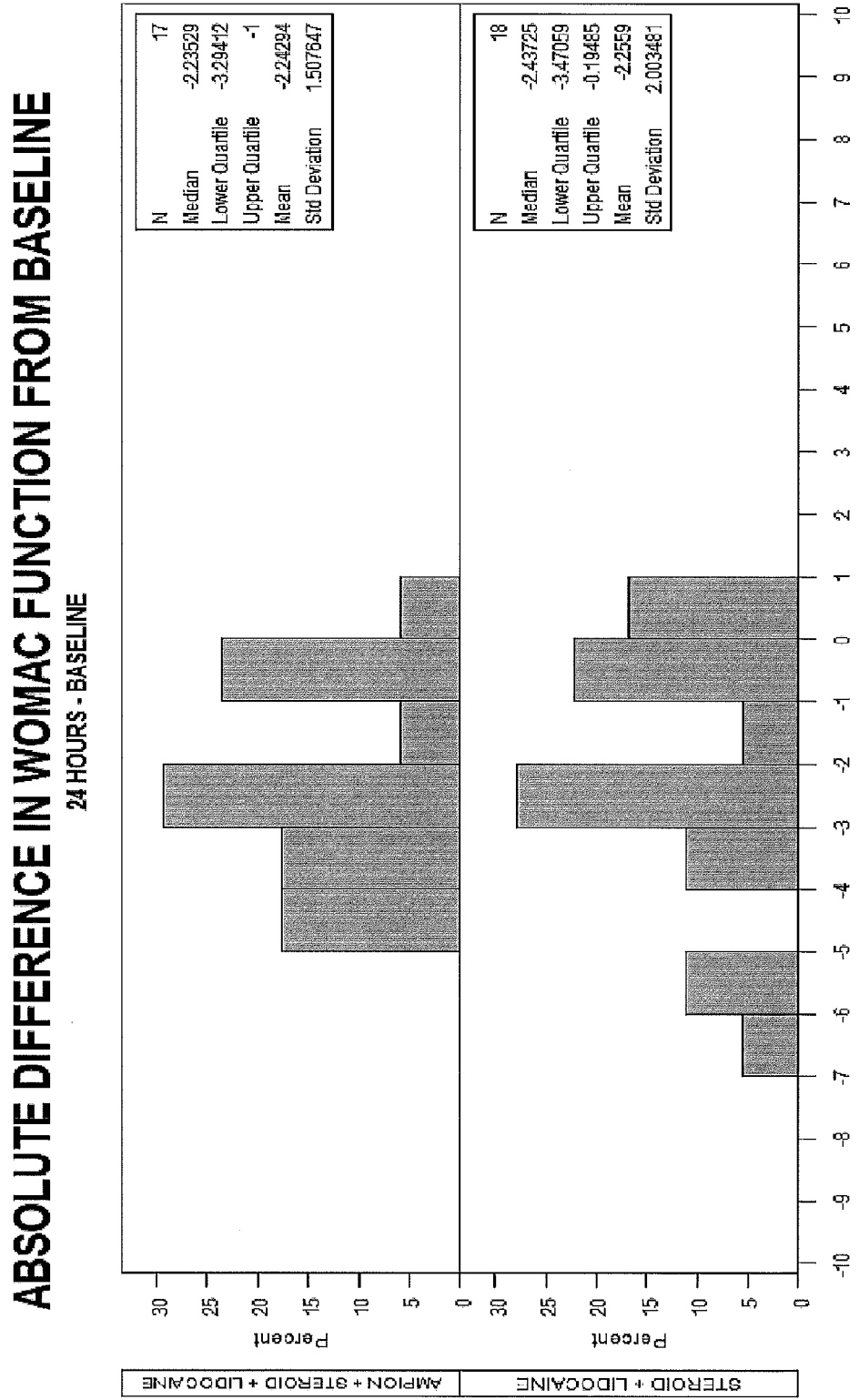
FIG. 5A shows the absolute difference in WOMAC function subscores at 24 hours for the treatment described in FIG. 1.

The data were analyzed using the Student's t-test: mean (SD) difference between treatment groups A and C for the following:
  Mean change in pain NRS at 6 hours, 24 hours and 72 hours (FIG. 1);
  Mean change in WOMAC pain subscores at 24 hours and 72 hours (FIGS. 3A and 3B);
  Mean change in WOMAC function subscores at 24 hours and 72 hours (FIGS. 5A and 5B); and
  Mean change in WOMAC stiffness subscores at 24 hours and 72 hours (FIGS. 4A and 4B).

Also, repeated measures ANOVA were calculated: mean (SD) difference between treatment groups A and C for mean change in pain NRS with time (FIG. 2).

Results

Figure 6:
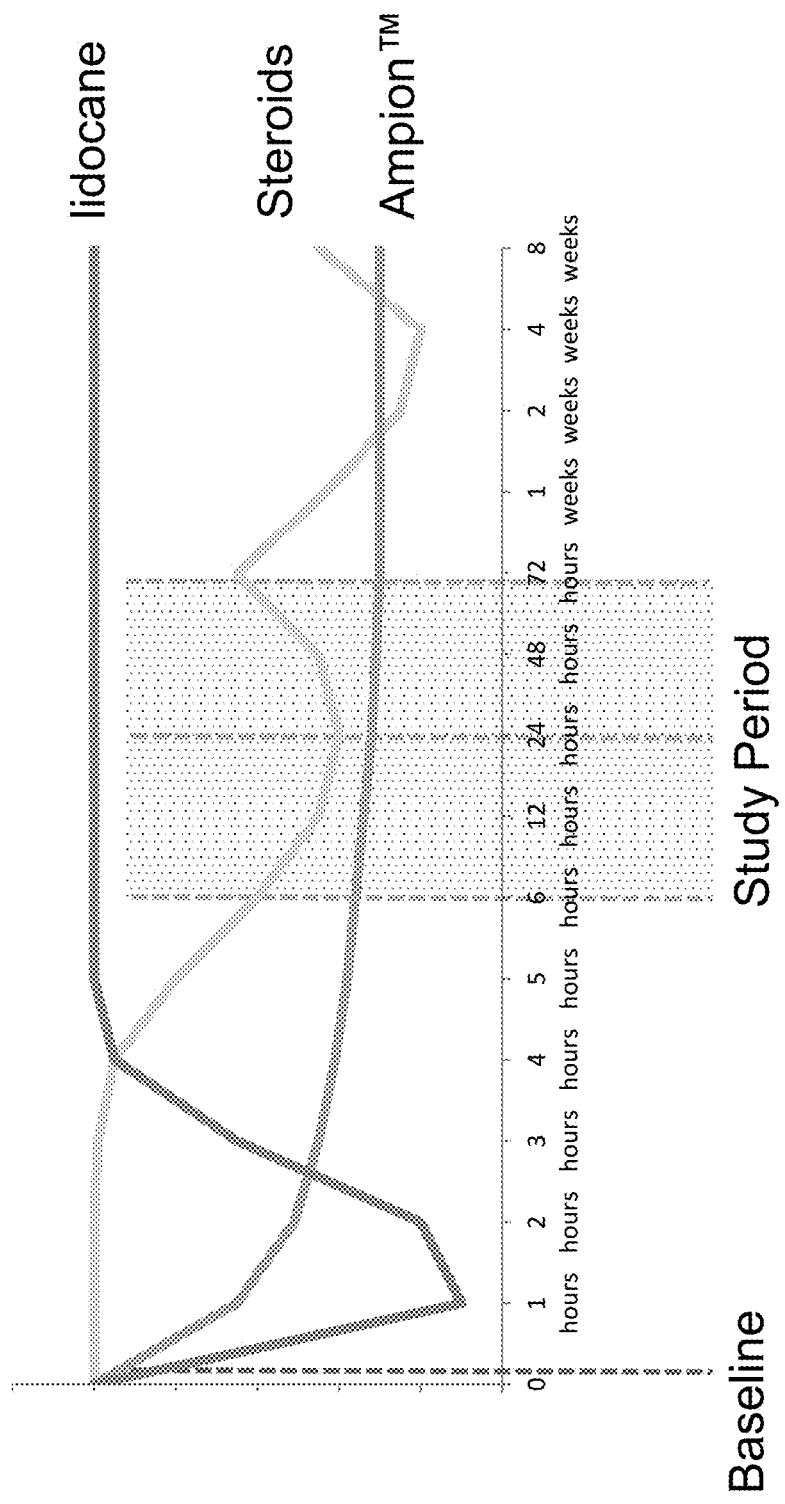
FIG. 6 shows a potential steroid time course.

Results are presented in FIGS. 1-6, Tables 2 and 3 and are summarized here:
  A trend in improvement in pain NRS with the <5000 MW Fraction (Ampion™) was observed. This trend increased with time versus steroids and demonstrates that the effects of the <5000 MW Fraction are long lasting.
  WOMAC—no differences were observed in the three subscores analyzed.
  The <5000 MW Fraction does not increase adverse events.
  Data on rescue medications and range of motion were only collected in a small percentage of patients and were not analyzed.
  Steroid Potential Time course is shown in FIG. 6. The onset of steroids efficacy is rapid: 12-24 hours maximal effect is reached in 1 week and lasts 4 weeks (Ann Rheum Dis 2004; 63:478-482). Short term pain increases from baseline through day 3 and decreases afterwards (Am J. Orthop. 2007 March; 36(3): 128-31).

TABLE 2

| | Baseline Efficacy Variables, mean (SD) | | |
|---|---|---|---|
| Efficacy Variable | Ampion ™ + Steriod + lidocaine | Steroid + lidocane | T-test p value |
| Pain NRS | 4.29 (2.28) | 3.61 (1.69) | 0.32 |
| WOMAC Pain | 4.09 (1.95) | 3.99 (2.07) | 0.91 |
| WOMAC Stiffness | 3.86 (1.78) | 3.93 (2.05) | 0.54 |

TABLE 2-continued

Baseline Efficacy Variables, mean (SD)

| Efficacy Variable | Ampion ™ + Steriod + lidocaine | Steroid + lidocane | T-test p value |
|---|---|---|---|
| WOMAC Function | 5.15 (2.10) | 4.69 (2.26) | 0.89 |

Ampion + Steroid + lidocane: n = 20, safety population; n = 17, efficacy analysis population
Steroid + lidocane: n = 20, safety population; n = 18, efficacy analysis population

TABLE 3

Mean Change in Pain NRS, mean (SD)

| Time | Ampion ™ + Steriod + lidocaine | Steroid + lidocane | T-test p value |
|---|---|---|---|
| 6 hours | −2.31 (2.36) | −2.06 (1.86) | 0.73 |
| 24 hours | −2.12 (1.58) | −1.61 (2.15) | 0.43 |
| 72 hours | −2.50 (1.83) | −1.82 (1.74) | 0.30 |

Example 2

A clinical trial was performed to investigate the effect of intra-articular knee injection of the <5000 MW Fraction (also referred to herein as "Ampion™") for improving joint function and reducing the pain of osteoarthritis of the knee in adults with symptomatic primary knee osteoarthritis. A randomized, placebo-controlled, double-blind, parallel study with 43 evaluable subjects was chosen as the appropriate design to estimate the treatment effect and safety of the <5000 MW Fraction when it was injected into the study knee.

Study Drug 2 arms; each subject received a single 4 ml injection in one knee with one of either Amipon™ or saline.

Study Population

The study population was 43 patient, male or female 40-83 years old (average 63.0, standard deviation (SD) 9.6) 28 were male and 15 were female. All subjects were Caucasian. The subjects' height ranged from 162 to 192 cm (average 175.3, SD 8.1) with weight at screening ranging from 56 to 117 kg (average 88.8, SD 13.89). The subjects were fully ambulatory, with symptomatic primary knee osteoarthritis for more than 6 months prior to screening with Kellgren Lawrence Grade II or III (indicating mild or moderate osteoarthritis). Grade II for 6 subjects and Grade III for 36 subjects. One subject did have Grade IV. If both knees of a subject were osteoarthritic, one knee was selected for study while the other knee received standard of care.

Exclusion Criteria:

The following is the exclusion criteria for the study population:

1. Unfit as a result of medical review and screening investigation
2. A history of allergic reactions to albumin
3. A history of allergic reactions to excipients in 5% human albumin
4. Any intra-articular or local periarticular injection, injection or surgery to the index knee (previous 6 months)
5. Operative arthroscopy (previous 3 months)
6. Surgical procedure to the index knee other than arthroscopy (previous 12 months)
7. Any investigational knee products (previous 12 months)
8. Kellgren Lawrence Grade I or IV (doubtful or severe) osteoarthritis of the knee.
9. Inflammatory or crystal arthropathies, acute fractures, severe loss of bone density, bone necrosis.
10. Isolated patella-femoral syndrome or chondromalacia.
11. Any other disease or condition interfering with the free use and evaluation of the index knee
12. Major injury to the index (previous 12 months)
13. Severe hip osteoarthritis ipsilateral to the index knee.
14. Any pain that could interfere with the assessment of index knee pain
15. Any pharmacological or non-pharmacological treatment started or changed (previous 4 weeks)
16. Use of a. any topical treatment (previous 48 h,) b. All analgesics and NSAIDs except paracetamol (previous 48 h), c. Anticoagulant therapy (previous 48 h) d. Any systemic steroid treatments (previous 14 days), e. All immunosuppressives within a period of 5 times the drug's half life prior to randomization, f. corticosteroids >10 mg prednisolone equivalent per day (previous 30 days), g. Any albumin treatment (previous 3 months)
17. Female subjects who are pregnant or lactating.
18. Female subjects of childbearing potential who have a positive pregnancy test on Day 1 prior to treatment.

Study Assessment

The study consisted of a three week screening period and an 84 day study participation period. Follow-up assessments were performed at 6 hours, 24 hours and 72 hours post injection. Subjects were contact by telephone at Day 8, Day 30 and Day 84 to evaluate overall pain and mobility and to monitor adverse events. The subjects were offered the option of intra-articular betamethasone injection to the investigative knee for pain relief after Day 8, if deemed necessary following an assessment by the investigator.

Primary Outcome

The pain numerical rating scale (NRS) in the study knee was completed at pre-dose (pre-injection baseline), 6 hours post-dose on Day 1, 24 hours post-dose on Day 2, 72 hours post-dose on Day 4, and at Day 8, Day 30 and Day 84 post-dose (EOS or End-of-study). The pain NRS is a numerical rating of 0-10, with 0 being no pain, 5 being moderate pain and 10 being worst possible pain.

Safety Endpoints

The safety endpoints of the study were incidence of adverse events, vital signs at pre-dose and study Day 4, twelve lead ECG readings at screening and 24 hours post-dose, and clinical blood safety tests (biochemical and hematology) assessed at screening and 24 hours post-dose.

Secondary Endpoints

The secondary endpoints of the study were percent responders at Day 30 and Day 84, defined as an improvement in pain NRS of 2 or more points, the change from pre-injection baseline in WOMAC Osteoarthritis Index 3.1 (complete scale, pain subscore, stiffness subscore and function subscore) at 24 and 72 hours after intra-articular injection, the change from pre-injection baseline for requirement for rescue medications (paracetamol) to 24 hours and 72 hours after intra-articular injection and changes over time in mobility at Day 8, Day 30 and Day 84 post-dose compared with pre-dose and the immediate post-dose period.

Intent to Treat (ITT) and Safety Population

Study participants who were randomized and received at least one dose of the study medication. ITT refers to subjects that met inclusion/exclusion criteria.

Per Protocol Population

Study participants in the ITT set whose pre-dose pain score did not violate inclusion/exclusion criteria.

Efficacy Population

Study participants in the pre-protocol population who did not receive rescue medication between 8 and 30 days.

Statistical Analyses

Primary: Analysis of covariance (ANCOVA) model to examine the mean (SD) difference between treatment groups for mean change in pain at Day 30 and Day 84 (EOS), adjusted for baseline pain NRS.

Additional: $X^2$ test for differences in percent responders. Cochran-armitage trend test for differences in clinically significant improvements. Student's t-test: mean (SD) difference in pain NRS at 30 days.

Safety Analysis:

Adverse events and serious adverse events were listed by subject. Summaries were presented by treatment of adverse events classified by MedDRA System Organ Class and Preferred Term, for overall incidence and by severity and relationship to study medication. Incidence of treatment-emergent adverse events were compared between treatment groups. All clinical safety and tolerability data was listed for each subject and summarized by treatment. Vital signs and ECG parameters were tabulated and summarized by treatment. Laboratory values were listed, along with comments as to clinical significance for values outside the laboratory's normal ranges. Changes from screening were assessed for clinical significance.

Results:

TABLE 4

Population

| Analysis Set | Study Size (n) | Ampion ™ (n) | Saline (n) |
|---|---|---|---|
| Safety Set | 43 | 22 | 21 |
| ITT Set | 43 | 22 | 21 |
| Per-protocol Set[a] | 41 | 20 | 21 |
| Efficacy evaluable Set[b] | 32 | 17 | 15 |

[a] 2 subjects in the Ampion ™ group had baseline pain NRS < 4 points
[b] 5 subjects in the Ampion ™ group and 6 subjects in the saline group required rescue medication Use of Rescue Medications Betamethasone injection: there was no apparent difference between the use of betamethasone injections between subjects who received Ampion™ (5 of 22 subjects, 23%) compared with subjects who received saline (6 of 21 subjects, 29%).

Rescue medications (paracetamol): rescue medication for pain relief in the study knee within 24 hours of injection occurred in a similar number of subjects receiving Ampion™ (6 of 22 subjects) compared with subjects receiving saline (6 of 21 subjects), with similar mean doses of paracetamol used in each of the treatment groups.

Efficacy Results:

TABLE 5

Pain NRS by treatment, mean (SD) pre-protocol population:

| Treatment | Pre-dose | 6 h Post dose | 24 h Post dose | 72 h Post dose | Day 8 Post dose | Day 30 Post dose | Day 84 Post dose |
|---|---|---|---|---|---|---|---|
| Ampion ™ | 4.70 (0.7) | 2.00 (1.3) | 3.20 (1.5) | 2.60 (2.1) | 2.90 (2.1) | 2.90 (1.8) | 3.21 (1.8) |
| Saline | 5.29 (1.4) | 2.67 (1.9) | 3.00 (1.7) | 2.86 (2.1) | 3.33 (1.9) | 3.86 (2.2) | 4.81 (2.3) |

TABLE 6

Least Squares (LS) Mean Change in Pain NRS: per-protocol population

| Treatment | 6 h Post dose | 24 h Post dose | 72 h Post dose | Day 8 Post dose | Day 30 Post dose | Day 84 Post dose |
|---|---|---|---|---|---|---|
| D (Ampion ™) | −3.06 | −1.69 | −2.31 | −2.00 | −2.16 | −1.60 |
| E (Saline) | −2.28 | −2.11 | −2.22 | −1.76 | −1.09 | −0.36 |
| P value | 0.15 | 0.42 | 0.89 | 0.71 | 0.12 | 0.07 |

Scale: −10 = largest possible improvement in pain from baseline, 10 = smallest possible improvement (largest increase) in pain from baseline.
Day 1: 6 hours post-dose
*adjusted for baseline pain NRS

TABLE 7

LS Mean Change in Pain NRS: efficacy evaluable population

| Treatment | 6 h Post dose | 24 h Post dose | 72 h Post dose | Day 8 Post dose | Day 30 Post dose | Day 84 Post dose |
|---|---|---|---|---|---|---|
| D (Ampion ™) | −2.91 | −1.99 | −2.94 | −2.45 | −2.29 | −2.22 |
| E (Saline) | −2.62 | −2.61 | −2.79 | −2.22 | −1.17 | −0.46 |
| P value | 0.62 | 0.19 | 0.79 | 0.71 | 0.19 | 0.04 |

Scale: −10 = largest possible improvement in pain from baseline, 10 = smallest possible improvement (largest increase) in pain from baseline.
Day 1: 6 hours post-dose
*adjusted for baseline pain NRS Percent responders at Day 84 (EOS): per-protocol population (see Table 8)

Responder: decrease in Day 84 pain NRS of −2 to −10 points (with −10 being the largest possible improvement in pain).

Non-responder: decrease in pain at Day 84 of −1 to 10 (with 10 being the largest possible increase in pain).

TABLE 8

Trends in pain at 30 days from baseline, by treatment group:

| Treatment | Non-Responder | Responder | P value |
|---|---|---|---|
| Ampion ™ | 47.4% | 52.6% | 0.06 |
| Saline | 76.2% | 23.8% | |

Percent responders at Day 84 (EOS): efficacy evaluable population (see Table 9)

Responder: decrease in Day 84 pain NRS of −2 to −10 points (with −10 being the largest possible improvement in pain).

Non-responder: decrease in pain at Day 84 of −1 to 10 points (with 10 being the largest possible increase in pain).

TABLE 9

Trends in pain at 30 days from baseline, by treatment group:

| Treatment | Non-Responder | Responder | P value |
|---|---|---|---|
| Ampion ™ | 35.7% | 64.3% | 0.10 |
| Saline | 66.7% | 33.3% | |

Figure 7:
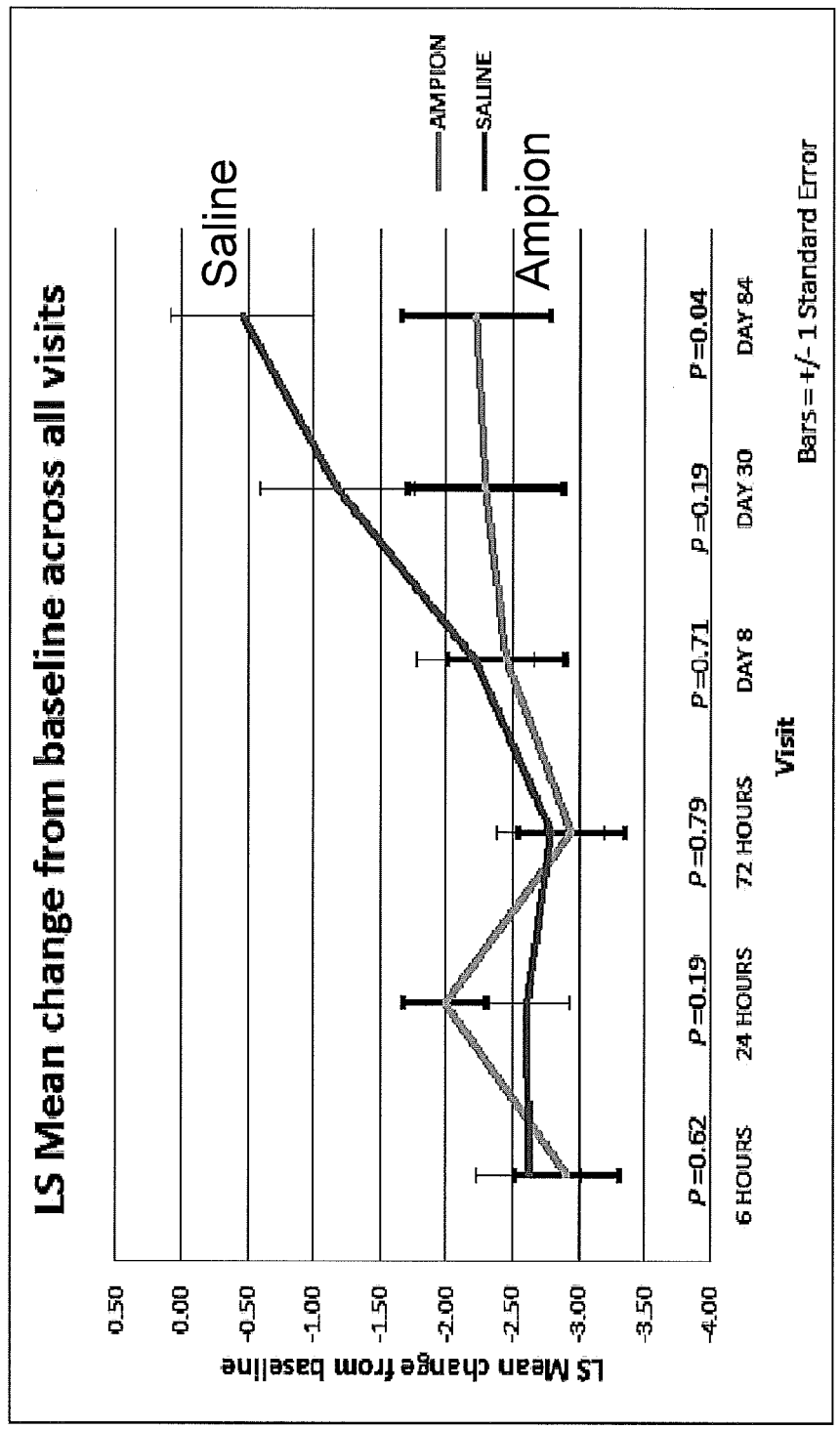
FIG. 7 shows the mean change from baseline across all subject visits for the treatment described in FIG. 1. ("LS" stands for least squares)

Summary of Findings: Efficacy:

Overall pain (as assessed by the pain numerical rating score) and WOMAC scores were reduced post-dose for each of the treatment groups for the duration of the study (p<0.05), except placebo at Day 84. In addition, there was a trend in a significant difference between changes from baseline at Day 30 and at Day 84 for subjects who received Ampion™ compared to subjects who received saline placebo (Day 30:

p=0.12; Day 84: p=0.07). This trend became statistically significant in subjects who did not receive rescue medication (p=0.04). There was a trend towards a higher percentage of responders at the end of the study (Day 84) for subjects receiving Ampion™ vs. Placebo (p=0.06). Use of paracetamol rescue medication up to 72 hours post-dose was highest in the Treatment E group (saline). See FIG. 7.

Adverse Events (AEs)

Treatment-emergent AEs were reported for 20 of the 43 subjects (47%) following dose administration, with a total of 27 AEs. Commonly occurring AEs were headache and joint swelling and stiffness in the knee. Most subjects reported AEs classified as mild only (16 of 43 subjects, 37%). Only 4 subjects (9%) reported AEs of moderate severity:

Ampion™: Joint injury and hypertension
Saline: Back pain and vessel puncture site haematoma There were no apparent differences in the incidence of moderate AEs between subjects who received Ampion™ (2 subjects, 9%) compared with subjects who received saline (2 subjects, 10%). These AEs were all deemed to be probably not or definitely not related to study drug.

There were no AEs classified as severe.

AEs deemed to be related to study drug administration (possibly) were reported in 3 of 43 subjects (7%). There were no apparent differences in the incidence of related AEs between subjects who received Ampion™ (1 subject, 5%) compared with subjects who received saline (2 subjects, 10%):

a. Headache of mild severity which commenced 5 minutes after treatment administration and resolved 1.8 hours later (Ampion™)
b. Headache of mild severity which commenced 5 hours after treatment administration and resolved 0.5 hours later (saline)
c. Joint swelling of right knee (study knee) of mild severity which commenced 2.4 days after treatment administration and resolved 21 hours later (saline)

Overall, a higher proportion of treatment-emergent AEs were reported in subjects who received saline (12 subjects, 57%) compared with subjects who received Ampion™ (8 subjects, 36%). AEs deemed to be related to study drug administration (possibly) were reported in 3 of 43 subjects (7%) and included headache and joint swelling of the knee. There were no deaths or other serious AEs. There were no clear differences in safety as assessed by biochemistry clinical laboratory tests, vital signs, and ECG assessments between treatments.

Conclusions of Study:

Pain (as assessed by the pain numerical rating score) and WOMAC scores were reduced post-dose for each of the treatment groups for the duration of the study, except placebo at Day 84, with no significant differences between treatment groups. Despite a higher baseline pain NRS for the saline group compared to the Ampion™ group, there was a trend towards a long-term effect of study drug, with a higher percentage of subjects who responded at Day 84 for Ampion™ compared to saline. In subjects receiving Ampion™, overall pain was reduced post-dose for the duration of the study, whereas subjects receiving saline did not have a reduction in pain post-dose at Day 84. Use of paracetamol rescue medication up to 72 hours post-dose was highest in the Treatment E group (saline). Ampion™ was considered safe and well tolerated at the dose used in the study.

Example 3

This study demonstrates that DA-DKP and N-Acetyl Tryptophan (NAT) of the <5 kDa fraction of 5% HSA binds to collagen. In particular, at equimolar concentration, NAT binds more to oxidized collagen IV than DA-DKP.

Methods

Collagen source: 1 mg/ml Collagen IV form human placenta in 0.25% acetic acid (Sigma™). The collagen was oxidized with 500 µM $H_2O_2$ in 1×PBS for 1 hour at 37° C. The oxidized collagen IV (final=0.2 mg/ml) was then incubated with 2 µM DA-DKP or 2 µM NAT in PBS for 1 hour at 37° C. At the end of the incubation, the <5 kDa fraction was isolated by a VIVASPIN® 2 microcentrifugal filter having a molecular weight cutoff of 5,000. The <5 kDa fraction was analyzed for DA-DKP and/or NAT content using a liquid chromatograph-mass spectrometery (LCMS) method for DA-DKP analysis.

The results of the analyses are shown in Table 10.

TABLE 10

Potential Binding of NAT and DA-DKP to $H_2O_2$ treated Human Collagen

| Sample | Average % decrease | Standard Deviation |
|---|---|---|
| 2 µM DA-DKP + Collagen IV | 26.0% | 4.2% |
| 2 µM DA-DKP + Collagen IV w/2 µM NAT | 25.6% | 5.7% |
| 2 µM NAT + Collagen IV | 48.9% | 1.3% |
| 2 µM NAT + Collagen IV w/2 µM DA-DKP | 28.7% | 9.4% |

The results provided in Table 10 demonstrate that DA-DKP and NAT bind to oxidized forms of collagen and hence block the oxidized sites from triggering immune cell activation.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed:

1. A method of reducing the pain associated with osteoarthritis of the knee comprising administering an intra-articular injection to a knee of an animal in need thereof, an effective amount of a pharmaceutical composition comprising an aspartic acid-alanine diketopiperazine (DA-DKP), in a concentration from about 50 µM to about 350 µM, wherein the composition further comprises N-acetyl-tryptophan (NAT) and caprylate and wherein the administration provides reduction in knee pain.

2. The method of claim 1 wherein the composition is administered no more frequently than once every six months, once every 5 months, once every 4 months, once every 3 months, or once every 2 months.

3. The method of claim 1, wherein the composition is a composition having a concentration of NAT and caprylate from about 4 mM to about 20 mM.

4. The method of claim 1, wherein the pharmaceutical composition further comprises a second drug selected from the group consisting of a steroid, lidocaine, and combinations thereof.

* * * * *